US007611832B2

(12) United States Patent
Adams et al.

(10) Patent No.: US 7,611,832 B2
(45) Date of Patent: Nov. 3, 2009

(54) HUMAN G PROTEIN-COUPLED RECEPTOR AND MODULATORS THEREOF FOR THE TREATMENT OF ISCHEMIC HEART DISEASE AND CONGESTIVE HEART FAILURE

(75) Inventors: John W. Adams, San Diego, CA (US); Daniel T. Connolly, Solana Beach, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/523,100

(22) PCT Filed: Jul. 25, 2003

(86) PCT No.: PCT/US03/23296

§ 371 (c)(1),
(2), (4) Date: Jan. 31, 2005

(87) PCT Pub. No.: WO2004/013285

PCT Pub. Date: Feb. 12, 2004

(65) Prior Publication Data

US 2005/0238579 A1 Oct. 27, 2005

Related U.S. Application Data

(60) Provisional application No. 60/400,774, filed on Aug. 1, 2002.

(51) Int. Cl.
*C12Q 1/00* (2006.01)
*C07K 14/705* (2006.01)
(52) U.S. Cl. ............................................ 435/4; 530/350
(58) Field of Classification Search ........................ None
See application file for complete search history.

(56) References Cited

U.S. PATENT DOCUMENTS 5,994,097 A 11/1999 Lal et al.
6,555,339 B1 * 4/2003 Liaw et al. ................. 435/69.1

FOREIGN PATENT DOCUMENTS

| WO | WO 99/10491 A1 | 3/1999 |
|---|---|---|
| WO | WO 00/22129 A1 | 4/2000 |
| WO | WO 01/83550 A2 | 11/2001 |
| WO | WO 01/83550 A3 | 11/2001 |
| WO | WO 02/06445 A2 | 1/2002 |
| WO | WO 02/061432 A2 | 8/2002 |
| WO | WO 03/065984 A2 | 8/2003 |
| WO | WO 03/065984 A3 | 8/2003 |
| WO | WO 2004/013285 A2 | 2/2004 |
| WO | WO 2007/047520 A1 | 4/2007 |

OTHER PUBLICATIONS

Database EMBL Sep. 19, 2001, "*Rattus norvegicus* clone CH230-11G1, *Sequencing in Progress*, 1 ordered piece." Database accession No. AC096185 *sequence NT 35762 to 36198.
Okazaki et al. Analysis of the mouse transcriptome based on functional annotation of 60,770 full-length cDNAs. Nature. Dec. 5, 2002, vol. 420, No. 6915, pp. 563-573.
Database NCBI on STN, An AAB63815, Gattung, S. "Putative G protein-coupled receptor [*Homo sapiens*]". Feb. 4, 2000, NCBI protein database, pp. 1-2.
O'Dowd et al. Cloning and chromosomal mapping of four putative novel human G-protein-coupled receptor genes. Gene (1997) 187:75-81.
Palczewski et al., "*Crystal structure of rhodopsin: A G protein-coupled receptor*", Science 2000 289:739-45.
Shin N. et al., *Molecular modeling and site-specific mutagenesis of the histamine-binding site of the histamine H4 receptor.* Mol Pharmacol. 2002 62:38-47.
Chung Da et al., "Mutagenesis and peptide analysis of the DRY motif in the alpha2A adrenergic receptor: evidence for alternate mechanisms in G protein-coupled receptor" Biochem Biophys Res Commun. 2002 293:1233-41.
Mouledous et al., "*Functional inactivation of the nociceptin receptor by alanine substitution of glutamine 286 at the C terminus of transmembrane segment VI: evidence from a site-directed mutagenesis study of the ORL1 receptor transmembrane-binding domain*" Mol Pharmacol. 2000 57:495-502.
Krasnoperov et al., "*Structural requirements for alpha-latrotoxin binding and alpha-latrotoxin-stimulated secretion. A study with calcium-independent receptor of alpha-latrotoxin (CIRL) deletion mutants*" J Biol Chem. 1999 274:3590-6.
Hurley et al., "*Structure-function studies of the eighth hydrophobic domain of a serotonin receptor*" J Neurochem. 1999 72:413-21.
Akal-Strader et al., *Residues in the first extracellular loop of a G protein-coupled receptor play a role in signal transduction.* J Biol Chem. 2002 277:30581-90.
Yang et al., "*Molecular determinants of human melanocortin-4 receptor responsible for antagonist SHU9119 selective activity*" J Biol Chem. 2002 277:20328-35.

(Continued)

*Primary Examiner*—Ruixiang Li
(74) *Attorney, Agent, or Firm*—James S. Keddie; Carol L. Francis; Bozicevic, Field & Francis LLP

(57) ABSTRACT

The present invention relates to methods of identifying whether a candidate compound is a modulator of an orphan G protein-coupled receptor (GPCR). Preferably the GPCR is human. In some embodiments, the GPCR is expressed endogenously by cardiomyocytes. In some embodiments, the GPCR is coupled to Gi and lowers the level of intracellular cAMP. In some embodiments, overexpression of the GPCR promotes survival of cardiomyocytes. In some embodiments, overexpression of the GPCR rescues cardiomyoctes from hypoxia/reoxygenation induced apoptosis. In some embodiments, the GPCR is down-regulated in individuals with congestive heart failure. Agonists of the invention are envisioned to be useful as therapeutic agents for the treatment of ischemic heart disease, including myocardial infarction, post-myocardial infarction remodeling, and congestive heart failure.

14 Claims, 11 Drawing Sheets

OTHER PUBLICATIONS

Ulloa-Aguirre et al., "*Structure-activity relationships of G protein-coupled receptors*" Arch Med Res. 1999 30:420-35 (Review).

Chollet et al., "*Biophysical approaches to G protein-coupled receptors: structure, function and dynamics*" J Comput Aided Mol Des. 1999 13:209-19 (Review).

Gimpl et al., "*The oxytocin receptor system: structure, function, and regulation*," Physiol Rev. 2001 81:629-83 (Review).

Bai et al., "*Structure and function of the extracellular calcium-sensing receptor*," Int J Mol Med. 1999 4:115-25 (Review).

Olah et al., "*The role of receptor structure in determining adenosine receptor activity*," Pharmacol Ther. 2000 85:55-75 (Review).

Missale et al., "*Dopamine receptors: from structure to function*," Physiol Rev. 1998 78:189-225 (Review).

Sealfon et al., *Functional domains of the gonadotropin-releasing hormone receptor*, Cell Mol Neurobiol. 1995 15:25-42 (Review).

Filizola et al., "*BUNDLE: a program for building the transmembrane domains of G-protein-coupled receptors*," J Comput Aided Mol Des. 1998 12:111-8.

Orry et al., "*Modeling and docking the endothelin G-protein-coupled receptor*," Biophys J. 2000 79:3083-94.

Califano, "SPLASH: structural pattern localization analysis by sequential histograms," *Bioinformatics*. 2000 16:341-57.

Gouldson et al., "*Domain swapping in G-protein coupled receptor dimmers*," Protein Eng. 1998 11:1181-93.

Gouldson et al., "*Dimerization and domain swapping in G-protein-coupled receptors: a computational study*," Neuropsychopharmacology. 2000 23:S60-77.

Chen et al., "Alterations of gene expression in failing myocardium following left ventricular assist device support".

Bialik et al., "*The Mitochondrial Apoptotic Pathway is Activated by Serum and Glucose Deprivation in Cardiac Myocytes*," Circulation Research 1999:403-414.

Bonavita et al., "*H9c2 cardiac myoblasts undergo apoptosis in a model of ischemia consisting of serum deprivation and hypoxia: inhibition by PMA*," FEBS Letters 2003:85-91.

Ross, "*Pharmacodynamics Mechanisms of Drug Action and the Relationship Between Drug Concentration and Effect*," Goodman & Gilman's The Pharmacological Basis of Therapeutics 1996: 29-30.

Laughwitz et al., "*Blocking Caspase-Activated Apoptosis Improves Contractility in Failing Myocardium*," Human Gene Therapy, 2001: 2051-2056.

Katz et al., "*Heart Failure Pathophysiology, Molecular Biology and Clinical* Management," 2000: xiii-3.

Lee et al., "*Insulin Like Growth Factor I Improves Cardiovascular Function and Suppresses Apoptosis of Cardiomyocytes in Dilated Cardiomyopathy*," Endocrinology 1999: 4831-4840.

Adams et al., "*G-Proteins in growth and apoptosis: lessons from the heart*," Oncogene 2001:1626-1634.

Adams, et al. G-proteins in growth and apoptosis: lessons from the heart. Oncogene. 2001, vol. 20, No. 13, pp. 1626-1634.

Bialik, et al. The mitochondrial apoptotic pathway is activated by serum and glucose deprivation in cardiac myocytes. Circulation Research. 1999, vol. 85, No. 5, pp. 403-414.

Bonavita, et al. H9c2 cardiac myoblasts undergo apoptosis in a model of ischemia consisting of serum deprivation and hypoxia: inhibition by PMA. FEBS Letters. 2003, vol. 536, pp. 85-91.

Cerbai, et al. Isolated cardiac cells for electropharmacological studies. Pharmacological Research. 2000, vol. 42, No. 1, pp. 1-8.

Long, et al. Sympathetic modulation of the cardiac myocyte phenotype: studies with a cell-culture model of myocardial hypertrophy. Basic Research in Cardiology. 1992, vol. 87, Suppl 2, pp. 19-31.

Parker, T. Molecular biology of myocardial hypertrophy and failure: gene expression and trophic signaling. New Horizons. 1995, vol. 3, No. 2, pp. 288-300.

Schaub, et al. Various hypertrophic stimuli induce distinct phenotypes in cardiomyocytes. Journal of Molecular Medicine. 1997, vol. 75, pp. 901-920.

\* cited by examiner

In Situ Hybridization:
RUP41 Expression in Adult Rat Heart

GAPDH

ANF

RUP41 sense      antisense

Down-Regulation of RUP41 in
Hypertrophied Neonatal Rat Ventricular Myocytes

A.

B.

Down-Regulation of RUP41 in Mouse Hearts Subjected to Pressure Overload Hypertrophy Down-Regulation of RUP41 In NRVMs Subjected to Hypoxia

Down-Regulation of RUP41 In Humans with Congestive Heart Failure

A.

B.

RUP41 Couples to Gi in COS-7 cells
cotransfected with TSHR-A623I

Stimulated by 1µM forskolin

Adenovirus-Mediated Over-Expression Of RUP41 Promotes Survival of NRVMs

A.

B.

No Virus      AdRUP41

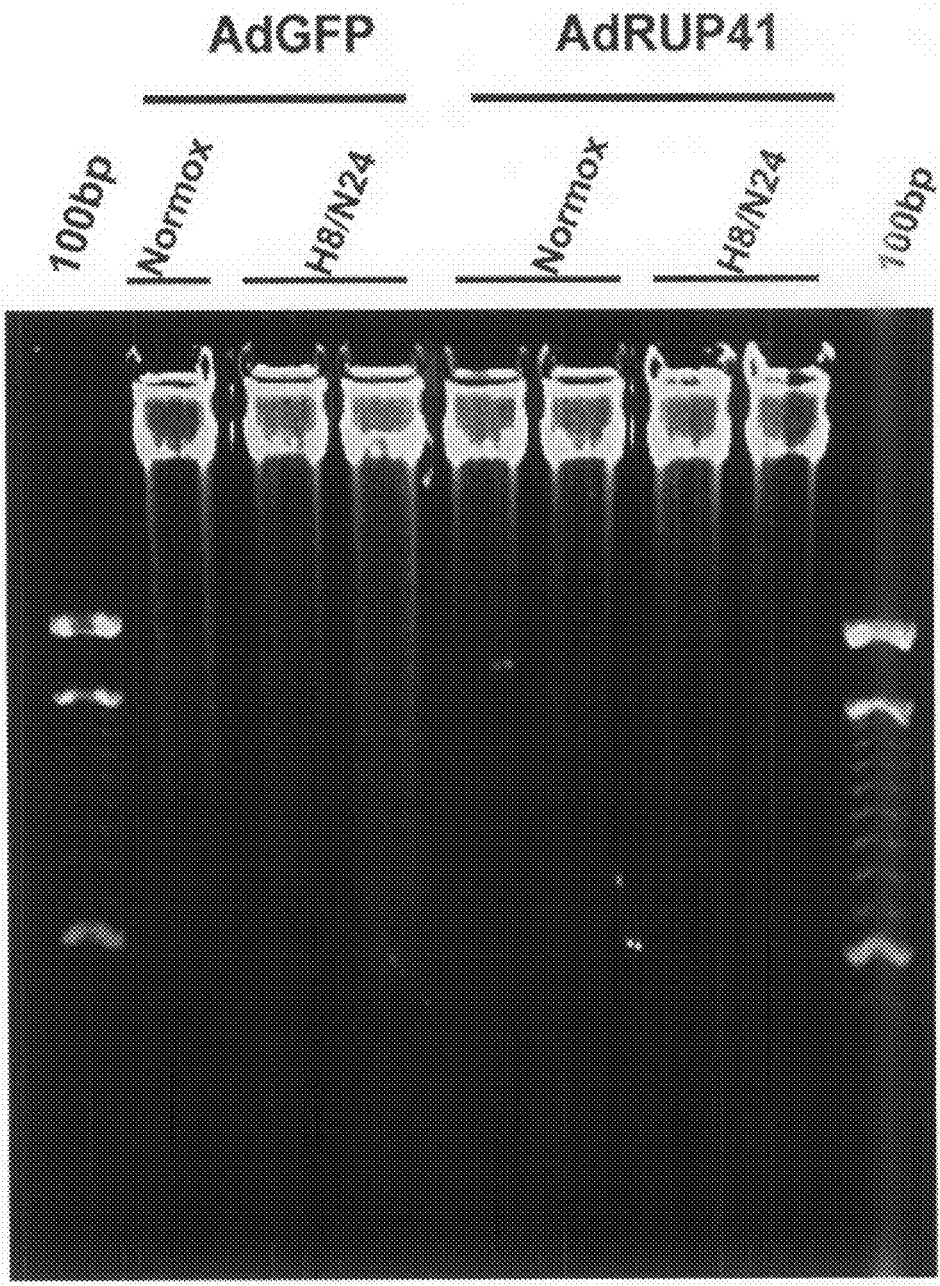

HUMAN G PROTEIN-COUPLED RECEPTOR AND MODULATORS THEREOF FOR THE TREATMENT OF ISCHEMIC HEART DISEASE AND CONGESTIVE HEART FAILURE

This patent application claims the benefit of priority from the following provisional application, filed via U.S. Express mail with the United States Patent and Trademark Office on the indicated date: U.S. Provisional No. 60/400,774, filed Aug. 1, 2002. The foregoing application is incorporated by reference herein in its entirety.

FIELD OF THE INVENTION

The present invention relates to methods of identifying whether a candidate compound is a modulator of an orphan G protein-coupled receptor (GPCR). Preferably the GPCR is human. In some embodiments, the GPCR is expressed endogenously by cardiomyocytes. In some embodiments, the GPCR is coupled to Gi and lowers the level of intracellular cAMP. In some embodiments, overexpression of the GPCR promotes survival of cardiomyocytes. In some embodiments, overexpression of the GPCR rescues cardiomyocytes from hypoxia/reoxygenation induced apoptosis. In some embodiments, the GPCR is down-regulated in individuals with congestive heart failure. Agonists of the invention are envisioned to be useful as therapeutic agents for the treatment of ischemic heart disease, including myocardial infarction, post-myocardial infarction remodeling, and congestive heart failure.

BACKGROUND OF THE INVENTION

A. Ischemic Heart Disease and Congestive Heart Failure

Congestive heart failure (CHF) affects nearly 5 million Americans with over 500,000 new cases diagnosed annually. By definition, CHF is a clinical syndrome in which heart disease reduces cardiac output, increases venous pressures, and is accompanied by molecular abnormalities that cause progressive deterioration of the failing heart and premature myocardial cell (myocyte) death (From; Heart Failure: Pathophysiology, Molecular Biology, and Clinical Management, Katz, A M, Lippincott Williams and Wilkins, 2000). In the adult heart, myocyte (cardiomyocyte) death is a critical element of the natural history of heart failure because the cells that are lost cannot be replaced. Because the 5-year survival rate, once heart failure becomes symptomatic, is less than 50%, any definition of heart failure that does not consider the molecular processes that accelerate myocardial death over-looks a major clinical feature of this syndrome. To this end, current research from many groups has focused on the molecular mechanisms and signaling pathways that regulate myocyte death and survival. Cell culture and small animal studies have clearly demonstrated that G-protein coupled receptors on cardiac myocytes are highly important regulators of cardiac contractile function and are also involved in the regulation of myocyte death and survival [for review, see Adams and Brown, Oncogene (2001) 20:1626-1634]. However, there are no drugs currently available in the clinic designed to inhibit cardiac myocyte death or directly activate survival pathways. Recently published evidence in mice and rats demonstrate that activation of survival pathways [Lee et al., Endocrinology (1999) 140:4831-40] or inhibitors of cardiac myocyte death pathways [Laugwitz et al., Hum Gene Ther (2001) 12:2051-63] significantly improves cardiac function and animal survival. Thus it is clear that similar therapeutic strategies for the treatment of human heart failure hold great promise.

B. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs. Receptors, including GPCRs, for which the endogenous ligand has been identified, are referred to as "known" receptors, while receptors for which the endogenous ligand has not been identified are referred to as "orphan" receptors.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

| | | |
|---|---|---|
| Claritin ® (allergies) | Prozac ® (depression) | Vasotec ® (hypertension) |
| Paxil ® (depression) | Zoloft ® (depression) | Zyprexa ® (psychotic disorder) |
| Cozaar ® (hypertension) | Imitrex ® (migraine) | Zantac ® (reflux) |
| Propulsid ® (reflux disease) | Risperdal ® (schizophrenia) | Serevent ® (asthma) |
| Pepcid ® (reflux) | Gaster ® (ulcers) | Atrovent ® (bronchospasm) |
| Effexor ® (depression) | Depakote ® (epilepsy) | Cardura ® (prostatic ypertrophy) |
| Allegra ® (allergies) | Lupron ® (prostate cancer) | Zoladex ® (prostate cancer) |
| Diprivan ® (anesthesia) | BuSpar ® (anxiety) | Ventolin ® (bronchospasm) |
| Hytrin ® (hypertension) | Wellbutrin ® (depression) | Zyrtec ® (rhinitis) |
| Plavix ® (MI/stroke) | Toprol-XL ® (hypertension) | Tenormin ® (angina) |
| Xalatan ® (glaucoma) | Singulair ® (asthma) | Diovan ® (hypertension) |
| Harnal ® (prostatic hyperplasia) | | |

(Med Ad News 1999 Data).

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

The present invention relates to an orphan GPCR designated herein as RUP41. RUP41 is related to GPR22 (GenBank® Accession No. U66581).

RUP41 is expressed endogenously by cardiac myocytes (cardiomyocytes). The expression profile of human RUP41 was determined by Affymetrix gene chip and verified by multi-tissue dot blot and Northern blot. Partial coding sequence for rat ortholog of RUP41, amplified from genomic DNA, has been identified and is disclosed. This fragment of the rat RUP41 polynucleotide sequence is 97% identical to the published mouse RUP41 polynucleotide sequence (XM_137998). RUP41 is disclosed herein to be coupled to Gi, resulting in inhibition of adenylyl cyclase and suppression of cAMP production. It is further disclosed that expression of endogenous RUP41 levels in experimental models of ischemic and hypertrophic hearts is decreased. It is further disclosed that over-expression of RUP41 promotes survival of cardiomyocytes. The disclosed properties of RUP41 indicate that an agonist of RUP41 is likely to be useful for the treatment of heart diseases associated with cardiomyocyte apoptosis.

In part the present invention is directed to methods of identifying whether a candidate compound is a modulator of RUP41. In other some embodiments, the present invention is directed to methods of modulating the activity of RUP41, comprising the step of contacting RUP41 with a modulator of RUP41. In some embodiments, said modulator lowers the intracellular level of cAMP. In some embodiments, the modulator is an agonist.

In some embodiments, said contacting occurs in vitro. In some embodiments, RUP41 modulator is introduced into cell culture models of cardiomyocyte apoptosis in a method of determining whether said modulator is effective in inhibiting cardiomyocyte apoptosis. In some embodiments, said modulator lowers the intracellular level of cAMP. In some embodiments, the modulator is an agonist.

In some embodiments, said contacting occurs in vivo. In some embodiments, RUP41 modulator is administered to mice and rats undergoing surgical models of ischemic heart disease and heart failure in a method of determining whether said modulator is effective in reducing the pathology associated said ischemic heart disease and heart failure. In yet other some embodiments, RUP41 modulator is administered to animals subjected to experimental myocardial infarction in a method of determining whether said modulator has benefit for cardiac remodeling and function. In some embodiments, said modulator lowers the intracellular level of cAMP. In some embodiments, the modulator is an agonist.

Modulators of RUP41 are envisioned to be useful as therapeutic agents for the treatment of ischemic heart disease, including myocardial infarction, post-myocardial infarction remodeling, and congestive heart failure. In some embodiments, said modulator lowers the intracellular level of cAMP. In some embodiments, the modulator is an agonist.

Polynucleotide sequence and the encoded polypeptide sequence for a first allele of human RUP41 are provided in the Sequence Listing as SEQ ID NO:1 and SEQ ID NO:2, respectively (the coding region for the polypeptide of SEQ ID NO:2 corresponds to nucleotides 237-1,538 of SEQ ID NO:1). Amino acid sequence for a second allele of human RUP41 polypeptide (GenBank® Accession No. AAB63815), comprising a single substitution of cysteine for lysine at amino acid position 425 of SEQ ID NO:2, is provided as SEQ ID NO:3 (the corresponding coding sequence is provided as nucleotides 79,559-80,860 of GenBank® Accession No. AC002381). Polynucleotide sequence and the encoded polypeptide sequence of mouse RUP41 are provided as SEQ ID NO:4 and SEQ ID NO:5, respectively. Polynucleotide sequence comprising partial coding sequence for rat RUP41 is disclosed as SEQ ID NO:6.

In a first aspect, the invention features a method of identifying whether a candidate compound is a modulator of a RUP41 GPCR, said receptor comprising a polypeptide selected from the group consisting of:
(a) the polypeptide of SEQ ID NO:2;
(b) the polypeptide of SEQ ID NO:3; and
(c) the polypeptide of SEQ ID NO:5;

or a fragment or variant thereof, wherein the receptor couples to a G protein, comprising the steps of:
(a') contacting the candidate compound with the receptor;
(b') determining whether the receptor functionality is modulated, wherein a change in receptor functionality is indicative of the candidate compound being a modulator of said GPCR.

The invention also relates to a method of identifying whether a candidate compound is a modulator of cardioprotection, comprising the steps of:

(a) contacting the candidate compound with a GPCR, said receptor comprising a polypeptide selected from the group consisting of:
  (i) the polypeptide of SEQ ID NO:2;
  (ii) the polypeptide of SEQ ID NO:3; and
  (iii) the polypeptide of SEQ ID NO:5;
  or a fragment or variant thereof, wherein the receptor couples to a G protein; and
(b) determining whether the receptor functionality is modulated;
wherein a change in receptor functionality is indicative of the candidate compound being a modulator of cardioprotection.

In some embodiments, said receptor comprises said polypeptide fragment selected from the group consisting of amino acids 2-433 of SEQ ID NO:2 and amino acids 2-433 of SEQ ID NO:3.

In some embodiments, said RUP41 GPCR is endogenous.

Allelic variants of RUP41 GPCR are envisioned to be within the scope of the invention.

Mammalian orthologs of human RUP41 polypeptide of SEQ ID NO:2 or SEQ ID NO:3 are envisioned to be within the scope of the invention. In some embodiments, said mammalian ortholog encompasses mouse RUP41, rat RUP41, pig RUP41, and non-human primate RUP41.

Variant polypeptides at least 90%, 91%, 92%, 93%, 94%, 95%, 96%, 97%, 98% or 99% identical to RUP41 polypeptide of SEQ ID NO:2, SEQ ID NO:3, or SEQ ID NO:5 are envisioned to be within the scope of the invention. In a particularly some embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402; the disclosures of which are incorporated by reference in their entirety]. Said variant polypeptide may comprise one or more amino acid deletions, insertions, and substitutions. A variant polypeptide selected from a constitutively activated version of RUP41 polypeptide of SEQ ID NO:2, SEQ ID NO:3, or SEQ ID NO:5 is envisioned to be within the scope of the invention. In some embodiments, said constitutively activated version of RUP41 polypeptide is the polypeptide of SEQ ID NO:2 or SEQ ID NO:3 wherein the phenylalanine at amino acid position 312 of SEQ ID NO:2 or SEQ ID NO:3 is substituted with lysine.

In some embodiments, said RUP41 GPCR is recombinant.

In some embodiments, said RUP41 GPCR comprises one or more epitope tag. In some embodiments, said epitope tag is hemagglutinin (HA) epitope tag. In some embodiments, said epitope tag is FLAG epitope tag. In some embodiments, said epitope tag is V5 epitope tag. Procedures for providing said HA, FLAG or V5 epitope tag are well known to those of ordinary skill in the art (Clontech, Palo Alto, Calif. and Invitrogen, Carlsbad, Calif., for example).

In some embodiments, said G protein modulates the level of intracellular cAMP. In some embodiments, said G protein is Gi.

In some embodiments, said determining is through the use of a Melanophore assay. In some embodiments, pigment aggregation is elevated. In some embodiments, pigment dispersion is reduced.

In some embodiments, said determining is through the measurement of the level of a second messenger selected from the group consisting of cyclic AMP (cAMP), cyclic GMP (cGMP), inositol triphosphate ($IP_3$), diacylglycerol (DAG) and $Ca^{2+}$. In some embodiments, said second messenger is cAMP. In some embodiments, the level of the cAMP is reduced. In some embodiments, said determining is carried out in COS-7 cells co-transfected with CART-TSH.

In some embodiments, said determining is carried out with membrane comprising said GPCR. In some embodiments, said membrane is made by homogenization of the cells with a Brinkman Polytron™. In some embodiments, said membrane preparation is made by homogenization with 3 bursts of 10-20 sec duration each of said polytron.

In some embodiments, said determining is through the measurement of an activity mediated by a reduction in intracellular cAMP level. In some embodiments, said activity is promotion of cell survival. In some embodiments, said cell is neonatal rat ventricular myocyte (NRVM). In some embodiments, said activity is cell rescue from hypoxia/reoxygenation induced apoptosis. In some embodiments, said cell is NRVM.

In some embodiments, said G protein is chimeric Gq(del)/Gi alpha subunit and said determining is through measurement of IP3 or $Ca^{2+}$.

In some embodiments, said determining is through the measurement of GTPγS binding to membrane comprising said GPCR. In further some embodiments, said GTPγS is labeled with [$^{35}$S].

In some embodiments, said contacting is carried out in the presence of a known ligand of the GPCR. In some embodiments, said known ligand is an agonist of the GPCR.

In some embodiments, said method further comprises the step of comparing the modulation of the receptor caused by the candidate compound to a second modulation of the receptor caused by contacting the receptor with a known modulator of the receptor.

In a second aspect, the invention features a modulator of a RUP41 GPCR or a modulator of cardioprotection identified according to a method of the first aspect.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µm, 6 µM, 7 µM, 8 µM, 9 µM, and 10 µM.

In some embodiments, said modulator lowers the level of intracellular cAMP.

In some embodiments, said modulator is an agonist.

In some embodiments, said modulator is selective.

In some embodiments, said modulator is orally bioavailable.

In some embodiments, said modulator is an antibody or derivative thereof comprising at least one binding domain.

In a third aspect, the invention features a method of modulating the activity of a RUP41 GPCR, said receptor comprising a polypeptide selected from the group consisting of:
  (a) the polypeptide of SEQ ID NO:2;
  (b) the polypeptide of SEQ ID NO:3; and
  (c) the polypeptide of SEQ ID NO:5;

or a fragment or variant thereof, wherein the receptor couples to a G protein, comprising the step of contacting the receptor with the modulator of the second aspect.

In some embodiments, said receptor comprises said polypeptide fragment selected from the group consisting of amino acids 2-433 of SEQ ID NO:2 and amino acids 2-433 of SEQ ID NO:3.

Allelic variants of RUP41 GPCR are envisioned to be within the scope of the invention.

Mammalian orthologs of human RUP41 polypeptide of SEQ ID NO:2 or SEQ ID NO:3 are envisioned to be within the scope of the invention. In some embodiments, said mammalian ortholog encompasses mouse RUP41, rat RUP41, pig RUP41, and non-human primate RUP41.

Variant polypeptides at least 90%, 91%, 92%, 93%, 94%, 95%, 96%, 97%, 98% or 99% identical to RUP41 polypeptide of SEQ ID NO:2, SEQ ID NO:3, or SEQ ID NO:5 are envisioned to be within the scope of the invention. In a particularly some embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402; the disclosures of which are incorporated by reference in their entirety]. Said variant polypeptide may comprise one or more amino acid deletions, insertions, and substitutions. Variant polypeptides that are constitutively activated versions of RUP41 polypeptide of SEQ ID NO:2, SEQ ID NO:3, or SEQ ID NO:5 are envisioned to be within the scope of the invention. In some embodiments, said constitutively activated version of RUP41 polypeptide is the polypeptide of SEQ ID NO:2 or SEQ ID NO:3 wherein the phenylalanine at amino acid position 312 of SEQ ID NO:2 or SEQ ID NO:3 is substituted with lysine.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said contacting comprises administration of the modulator to a membrane comprising the receptor.

In some embodiments, said contacting comprises administration of the modulator to a cell or tissue comprising the receptor.

In some embodiments, said contacting comprises administration of the modulator to an individual comprising the receptor.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In some embodiments, said method is used to identify whether the modulator has therapeutic efficacy for the prevention or treatment of a cardiovascular disorder selected from the group consisting of:
   (a) reduced cardiac output; and
   (b) increased venous pressures;

comprising the steps of:
   (a') administering said modulator to a cell culture model of cardiomyocyte apoptosis; and
   (b') determining whether said apoptosis is inhibited, wherein said determining is through a measurement selected from the group consisting of:
      (i) measurement of cell number;
      (ii) measurement of DNA fragmentation; and
      (iii) measurement of nuclear chromatin condensation;

wherein a determination of apoptosis inhibition is indicative of the modulator having said therapeutic efficacy.

In some embodiments, measurement of nuclear chromatin condensation is carried out using DAPI (4',6-Diamidino-2-phenylindole) stain.

In some embodiments, said method is used to identify whether the modulator has therapeutic efficacy for the prevention or treatment of an ischemic heart disease selected from the group consisting of:
   (a) myocardial infarction;
   (b) post-myocardial infarction remodelling; and
   (c) congestive heart failure;

comprising the steps of:
   (a') administering said modulator to a cell culture model of cardiomyocyte apoptosis; and
   (b') determining whether said apoptosis is inhibited, wherein said determining is through a measurement selected from the group consisting of:
      (i) measurement of cell number;
      (ii) measurement of DNA fragmentation; and
      (iii) measurement of nuclear chromatin condensation;

wherein a determination of apoptosis inhibition is indicative of the modulator having said therapeutic efficacy.

In some embodiments, measurement of nuclear chromatin condensation is carried out using DAPI (4',6-Diamidino-2-phenylindole) stain.

In some embodiments, said method is used to identify whether the modulator has therapeutic efficacy for the prevention or treatment of a cardiovascular disorder selected from the group consisting of:
   (a) reduced cardiac output; and
   (b) increased venous pressures;

comprising the steps of:
   (a') administering or not administering the modulator to a mouse or rat model of cardiovascular disorder; and
   (b') determining whether administration of the modulator has an effect selected from the group consisting of:
      (i) a decrease in cardiac hypertrophy;
      (ii) an increase in cardiac ejection volume;
      (iii) a decrease in ventricular chamber volume; and
      (iv) a decrease in cardiomyocyte apoptosis;

wherein a determination of said effect is indicative of said modulator having said therapeutic efficacy.

In some embodiments, said method is used to identify whether the modulator has therapeutic efficacy for the prevention or treatment of an ischemic heart disease selected from the group consisting of:
   (a) myocardial infarction;
   (b) post-myocardial infarction remodeling; and
   (c) congestive heart failure;

comprising the steps of:
   (a') administering or not administering the modulator to a mouse or rat model of ischemic heart disease; and
   (b') determining whether administration of the modulator has an effect selected from the group consisting of:
      (i) a decrease in cardiac hypertrophy;
      (ii) an increase in cardiac ejection volume;
      (iii) a decrease in ventricular chamber volume; and
      (iv) a decrease in cardiomyocyte apoptosis;

wherein a determination of said effect is indicative of said modulator having said therapeutic efficacy.

In some embodiments, said individual is in need of prevention of or treatment for a cardiovascular disorder selected from the group consisting of:
   (a) reduced cardiac output; and
   (b) increased venous pressures.

In some embodiments, said individual is in need of prevention of or treatment for an ischemic heart disease selected from the group consisting of:
   (a) myocardial infarction;
   (b) post-myocardial infarction remodeling; and
   (c) congestive heart failure.

In some embodiments, said individual is in need of a change in cardiovascular function selected from the group consisting of:
   (a) a decrease in cardiac hypertrophy;
   (b) an increase in cardiac ejection volume;
   (c) a decrease in ventricular chamber volume; and
   (d) a decrease in cardiomyocyte apoptosis.

In some embodiments, said individual is a mouse or rat genetically predisposed to a cardiovascular disorder selected from the group consisting of:
   (a) reduced cardiac output; and
   (b) increased venous pressures.

In some embodiments, said method is used to identify whether the modulator has therapeutic efficacy for the prevention or treatment of a cardiovascular disorder selected from the group consisting of:
   (a) reduced cardiac output; and
   (b) increased venous pressures;

comprising the steps of:
   (a') administering or not administering the modulator to said mouse or rat genetically predisposed to a cardiovascular disorder; and
   (b') determining whether administration of the modulator has an effect selected from the group consisting of:
      (i) a decrease in cardiac hypertrophy;
      (ii) an increase in cardiac ejection volume;
      (iii) a decrease in ventricular chamber volume; and
      (iv) a decrease in cardiomyocyte apoptosis;

wherein a determination of said effect is indicative of said modulator having said therapeutic efficacy.

In some embodiments, said individual is a mouse or rat genetically predisposed to an ischemic heart disease selected from the group consisting of:
   (a) myocardial infarction;
   (b) post-myocardial infarction remodeling; and
   (c) congestive heart failure.

In some embodiments, said method is used to identify whether the modulator has therapeutic efficacy for the prevention or treatment of an ischemic heart disease selected from the group consisting of:
   (a) myocardial infarction;
   (b) post-myocardial infarction remodeling; and
   (c) congestive heart failure;

comprising the steps of:
   (a') administering or not administering the modulator to said mouse or rat genetically predisposed to an ischemic heart disease; and
   (b') determining whether administration of the modulator has an effect selected from the group consisting of:
      (i) a decrease in cardiac hypertrophy;
      (ii) an increase in cardiac ejection volume;
      (iii) a decrease in ventricular chamber volume; and
      (iv) a decrease in cardiomyocyte apoptosis;

wherein a determination of said effect is indicative of said modulator having said therapeutic efficacy.

In a fourth aspect, the invention features a method of changing cardiovascular function in an individual in need of said change, comprising contacting a therapeutically effective amount of a modulator of the second aspect with a RUP41 GPCR, said receptor comprising a polypeptide selected from the group consisting of:
   (a) the polypeptide of SEQ ID NO:2;
   (b) the polypeptide of SEQ ID NO:3; and
   (c) the polypeptide of SEQ ID NO:5;

or an allelic variant thereof.

In some embodiments, said change in cardiovascular function is selected from the group consisting of:
   (a) a decrease in cardiac hypertrophy;
   (b) an increase in cardiac ejection volume;
   (c) a decrease in ventricular chamber volume; And
   (d) a decrease in cardiomyocyte apoptosis.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 $\mu$M to 100 $\mu$M. In some embodiments, said modulator has an EC50 or IC50 on human RUP41 GPCR of SEQ ID NO:2 or SEQ ID NO:3 of less than a value selected from the group consisting of 1 $\mu$M, 10 $\mu$M, 20 $\mu$M, 30 $\mu$M, 40 $\mu$M, 50 $\mu$M 60 $\mu$M, 70 $\mu$M, 80 $\mu$M, 90 $\mu$M, and 100 $\mu$M. In some embodiments, said modulator has an EC50 or IC50 on human RUP41 GPCR of SEQ ID NO:2 or SEQ ID NO:3 of less than a value selected from the interval of 1 $\mu$M to 10 $\mu$M. In some embodiments, said modulator has an EC50 or IC50 on human RUP41 GPCR of SEQ ID NO:2 or SEQ ID NO:3 of less than a value selected from the group consisting of 1 $\mu$M, 2 $\mu$M, 3 $\mu$M, 4 $\mu$M, 5 $\mu$M, 6 $\mu$M, 7 $\mu$M, 8 $\mu$M, 9 $\mu$M, and 10 $\mu$M.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said contacting is carried out through oral administration of said modulator.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a fifth aspect, the invention features a method of prevention of or treatment for a cardiovascular disorder in an individual in need of said prevention or treatment, comprising contacting a therapeutically effective amount of a modulator of the second aspect with a RUP41 GPCR, said receptor comprising a polypeptide selected from the group consisting of:

(a) the polypeptide of SEQ ID NO:2;
(b) the polypeptide of SEQ ID NO:3; and
(c) the polypeptide of SEQ ID NO:5;

or an allelic variant thereof.

In some embodiments, said cardiovascular disorder is selected from the group consisting of:

(a) reduced cardiac output; and
(b) increased venous pressures.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said contacting is carried out through oral administration of said modulator.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a sixth aspect, the invention features a method of prevention of or treatment for an ischemic heart disease in an individual in need of said prevention or treatment, comprising contacting a therapeutically effective amount of a modulator of the second aspect with a RUP41 GPCR, said receptor comprising a polypeptide selected from the group consisting of:

(a) the polypeptide of SEQ ID NO:2;
(b) the polypeptide of SEQ ID NO:3; and
(c) the polypeptide of SEQ ID NO:5;

or an allelic variant thereof.

In some embodiments, said ischemic heart disease is selected from the group consisting of:

(a) myocardial infarction;
(b) post-myocardial infarction remodelling; and
(c) congestive heart failure.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µm to 100 µM. In some embodiments, said modulator has an EC50 or IC50 on human RUP41 GPCR of SEQ ID NO:2 or SEQ ID NO:3 of less than a value selected from the group consisting of 1 µm, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said contacting is carried out through oral administration of said modulator.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a seventh aspect, the invention features a method of preparing a composition which comprises identifying a modulator of a RUP41 GPCR and then admixing a carrier and the modulator, wherein the modulator is identifiable by a method of the first aspect.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said modulator identifiable by a method of the first aspect is identified by a method of the first aspect.

In some embodiments, said modulator is a modulator of the second aspect.

In an eighth aspect, the invention features a pharmaceutical or physiologically acceptable composition comprising, consisting essentially of, or consisting of the modulator of the second aspect.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In a ninth aspect, the invention features a method of changing cardiovascular function comprising providing or administering to an individual in need of said change said pharmaceutical or physiologically acceptable composition of the eighth aspect, said change in cardiovascular function selected from the group consisting of:
 (a) a decrease in cardiac hypertrophy;
 (b) an increase in cardiac ejection volume;
 (c) a decrease in ventricular chamber volume; And
 (d) a decrease in cardiomyocyte apoptosis.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a tenth aspect, the invention features a method of treating a cardiovascular disorder comprising providing or administering to an individual in need of said treatment said pharmaceutical or physiologically acceptable composition of the eighth aspect, said cardiovascular disorder selected from the group consisting of:
 (a) reduced cardiac output; and
 (b) increased venous pressures.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In an eleventh aspect, the invention features a method of treating an ischemic heart disease comprising providing or administering to an individual in need of said treatment said pharmaceutical or physiologically acceptable composition of the eighth aspect, said ischemic heart disease selected from the group consisting of:
 (a) myocardial infarction;
 (b) post-myocardial infarction remodelling; and
 (c) congestive heart failure.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a twelfth aspect, the invention features a method of using a modulator of the second aspect for the preparation of a medicament for the treatment of a cardiovascular disorder in an individual.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said cardiovascular disorder is selected from the group consisting of:
 (a) reduced cardiac output; and
 (b) increased venous pressures.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a thirteenth aspect, the invention features a method of using a modulator of the second aspect for the preparation of a medicament for the treatment of an ischemic heart disease in an individual.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said ischemic heart disease is selected from the group consisting of:
(a) myocardial infarction;
(b) post-myocardial infarction remodelling; and
(c) congestive heart failure.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a fourteenth aspect, the invention features a method of making a knockout mouse, wherein said knockout mouse is predisposed to a cardiovascular disorder selected from the group consisting of:
(a) reduced cardiac output; and
(b) increased venous pressures;

comprising the step of knocking out a gene encoding the polypeptide of SEQ ID NO:5.

In some embodiments, said knocking out is cardiomyocyte selective.

In an fifteenth aspect, the invention features a method of making a knockout mouse, wherein said knockout mouse is predisposed to an ischemic heart disease selected from the group consisting of:
(a) myocardial infarction;
(b) post-myocardial infarction remodeling; and
(c) congestive heart failure;

comprising the step of knocking out a gene encoding the polypeptide of SEQ ID NO:5.

In some embodiments, said knocking out is cardiomyocyte selective.

In a sixteenth aspect, the invention features the knockout mouse of the fourteenth or fifteenth aspect.

In a seventeenth aspect, the invention features a method of using the knockout mouse of the sixteenth aspect to identify whether a candidate compound has therapeutic efficacy for the prevention or treatment of a cardiovascular disorder selected from the group consisting of:
(a) reduced cardiac output; and
(b) increased venous pressures;

comprising the steps of:
(a') administering or not administering the compound to the mouse; and
(b') determining whether administration of the modulator has an effect selected from the group consisting of:
(i) a decrease in cardiac hypertrophy;
(ii) an increase in cardiac ejection volume;
(iii) a decrease in ventricular chamber volume; and
(iv) a decrease in cardiomyocyte apoptosis;

wherein a determination of said effect is indicative of said modulator having said therapeutic efficacy.

In an eighteenth aspect, the invention features a method of using the knockout mouse of the sixteenth aspect to identify whether a candidate compound has therapeutic efficacy for the prevention or treatment of an ischemic heart disease selected from the group consisting of:
(a) myocardial infarction;
(b) post-myocardial infarction remodeling; and
(c) congestive heart failure;

comprising the steps of:
(a') administering or not administering the compound to the mouse; and
(b') determining whether administration of the modulator has an effect selected from the group consisting of:
(i) a decrease in cardiac hypertrophy;
(ii) an increase in cardiac ejection volume;
(iii) a decrease in ventricular chamber volume; and
(iv) a decrease in cardiomyocyte apoptosis;

wherein a determination of said effect is indicative of said modulator having said therapeutic efficacy.

In a nineteenth aspect, the invention features a method of making a knockout rat, wherein said knockout rat is predisposed to a cardiovascular disorder selected from the group consisting of:
(a) reduced cardiac output; and
(b) increased venous pressures;

comprising the step of knocking out a gene hybridizing at high stringency to the polynucleotide of SEQ ID NO:6.

In some embodiments, said knocking out is cardiomyocyte selective.

In a twentieth aspect, the invention features a method of making a knockout rat, wherein said knockout rat is predisposed to an ischemic heart disease selected from the group consisting of:
(a) myocardial infarction;
(b) post-myocardial infarction remodeling; and
(c) congestive heart failure;

comprising the step of knocking out a gene hybridizing at high stringency to the polynucleotide of SEQ ID NO:6.

In some embodiments, said knocking out is cardiomyocyte selective.

In a twenty-first aspect, the invention features the knockout rat of the nineteenth or twentieth aspect.

In a twenty-second aspect, the invention features a method of using the knockout rat of the twenty-first aspect to identify whether a candidate compound has therapeutic efficacy for the prevention or treatment of a cardiovascular disorder selected from the group consisting of:
(a) reduced cardiac output; and
(b) increased venous pressures;

comprising the steps of:
(a') administering or not administering the compound to the rat; and
(b') determining whether administration of the modulator has an effect selected from the group consisting of:
(i) a decrease in cardiac hypertrophy;
(ii) an increase in cardiac ejection volume;
(iii) a decrease in ventricular chamber volume; and
(iv) a decrease in cardiomyocyte apoptosis;

wherein a determination of said effect is indicative of said modulator having said therapeutic efficacy.

In a twenty-third aspect, the invention features a method of using the knockout rat of the twenty-first aspect to identify whether a candidate compound has therapeutic efficacy for the prevention or treatment of an ischemic heart disease selected from the group consisting of:
(a) myocardial infarction;
(b) post-myocardial infarction remodeling; and
(c) congestive heart failure;

comprising the steps of:

(a') administering or not administering the compound to the rat; and (b') determining whether administration of the modulator has an effect selected from the group consisting of:

(i) a decrease in cardiac hypertrophy;

(ii) an increase in cardiac ejection volume;

(iii) a decrease in ventricular chamber volume; and (iv) a decrease in cardiomyocyte apoptosis;

wherein a determination of said effect is indicative of said modulator having said therapeutic efficacy.

In a twenty-fourth aspect, the invention features an isolated rat RUP41 polynucleotide selected from the group consisting of:

(a) a polynucleotide comprising a contiguous span of at least 75 nucleotides of SEQ. ID. NO.:6;

(b) a polynucleotide comprising a contiguous span of at least 150 nucleotides of SEQ. ID. NO.:6;

(c) a polynucleotide comprising a contiguous span of at least 250 nucleotides of SEQ ID NO:6;

(d) a polynucleotide comprising a contiguous span of at least 350 nucleotides of SEQ. ID. NO.:6; and (e) a polynucleotide comprising a contiguous span of at least 500 nucleotides of SEQ. ID. NO.:6.

In some embodiments, said contiguous span does not include nucleotide 514 of SEQ ID NO:6.

In some embodiments, said isolated rat RUP41 polynucleotide comprises, consists essentially of, or consists of a nucleotide sequence that encodes endogenous rat RUP41 GPCR orthologous to human RUP41 GPCR of SEQ ID NO:2 or SEQ ID NO:3.

Variant polynucleotides at least 60%, 70%, 80%, 85%, 90%, 91%, 92%, 93%, 94%, 95%, 96%, 97%, 98% or 99% identical to a RUP41 polynucleotide of any one of (a) to (e) above is envisioned to be within the scope of the invention. In some embodiments, polynucleotide sequence homologies are evaluated using the Basic Local Alignment Search Tool ("BLAST"), which is well known in the art [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402; the disclosures of which are incorporated by reference in their entirety]. Said variant polynucleotide may comprise one or more nucleotide deletions, insertions, and substitutions.

In further embodiments, the invention features the complement of said isolated polynucleotide.

In a twenty-fifth aspect, the invention features a recombinant vector, said vector comprising an isolated polynucleotide of the twenty-fourth aspect. In some embodiments, said recombinant vector is an expression vector. In some embodiments, said expression vector is eukaryotic expression vector. Suitable expression vectors will be readily apparent to those of ordinary skill in the art.

In some embodiments, said recombinant vector is used in a method of transient or stable transfection. In some embodiments, said recombinant vector is used in a method of infection.

In some embodiments, said recombinant vector is a targeting vector used in a method of inactivating RUP41 gene.

In some embodiments, said recombinant vector is isolated.

In a twenty-sixth aspect, the invention features a prokaryotic or eukaryotic host cell comprising a recombinant vector of the twenty-fifth aspect. In some embodiments, the host cell is prokaryotic and is stably transformed using said recombinant vector. In some embodiments, the host cell is eukaryotic and is transiently transfected using said recombinant vector. In other further some embodiments, said host cell is eukaryotic and is stably transfected using said recombinant vector.

In some embodiments the host cell is eukaryotic, preferably, mammalian, and more preferably selected from the group consisting of 293, 293T, CHO and COS-7 cells. In some embodiments, the host cell is eukaryotic, more preferably melanophore. Other suitable host cells will be readily apparent to those of ordinary skill in the art.

In some embodiments, the host cell is a mammalian embryonic stem cell, or embryonic stem-like cell and said recombinant vector is used in a method of inactivating RUP41 gene. In some embodiments, the host cell is a mammalian embryonic somatic cell and said recombinant vector is used in a method of inactivating RUP41 gene.

A further embodiment includes a prokaryotic or eukaryotic host cell recombinant for a polynucleotide of the twenty-fourth aspect.

In some embodiments, the host cell is isolated.

In a twenty-seventh aspect, the invention features a GPCR Fusion Protein construct comprising a constitutively active G protein coupled receptor and a G protein, said receptor comprising a RUP41 polypeptide selected from the group consisting of:

(a) the polypeptide of SEQ ID NO:2;

(b) the polypeptide of SEQ. ID. NO:3; and (c) the polypeptide of SEQ ID NO:5;

or a fragment or variant thereof.

In some embodiments, said receptor comprises said polypeptide fragment selected from the group consisting of amino acids 2-433 of SEQ ID NO:2 and amino acids 2-433 of SEQ ID NO:3.

Allelic variants of RUP41 GPCR are envisioned to be within the scope of the invention.

Mammalian orthologs of human RUP41 polypeptide of SEQ ID NO:2 or SEQ ID NO:3 are envisioned to be within the scope of the invention. In some embodiments, said mammalian ortholog encompasses mouse RUP41, rat RUP41, pig RUP41, and non-human primate RUP41.

Variant polypeptides at least 90%, 91%, 92%, 93%, 94%, 95%, 96%, 97%, 98% or 99% identical to RUP41 polypeptide of SEQ ID NO:2, SEQ ID NO:3, or SEQ ID NO:5 are envisioned to be within the scope of the invention. In a particularly some embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402; the disclosures of which are incorporated by reference in their entirety]. Said variant polypeptide may comprise one or more amino acid deletions, insertions, and substitutions. Variant polypeptides that are constitutively activated versions of RUP41 polypeptide of SEQ ED NO:2, SEQ ID NO:3, or SEQ ID NO:5 are envisioned to be within the scope of the invention. In some embodiments, said constitutively activated version of RUP41 polypeptide is the polypeptide of SEQ ID NO:2 or SEQ ID NO:3 wherein the phenylalanine at amino acid position 312 of SEQ ID NO:2 or SEQ ID NO:3 is substituted with lysine.

In a twenty-eighth aspect, the invention features a method of identifying whether a candidate compound is a ligand of a RUP41 GPCR, said receptor comprising a polypeptide selected from the group consisting of:

(a) the polypeptide of SEQ ID NO:2;
(b) the polypeptide of SEQ ID NO:3; and
(c) the polypeptide of SEQ ID NO:5;

or a fragment or variant thereof, comprising the steps of:

(a') contacting said receptor with an optionally labeled known ligand to the receptor in the presence or absence of said candidate compound;

(b') detecting the complex between said known ligand and said receptor; and (c') determining whether less of said complex is formed in the presence of the candidate compound than in the absence of the candidate compound;

wherein said determination is indicative of the candidate compound being a ligand of said receptor.

In some embodiments, said receptor comprises said polypeptide fragment selected from the group consisting of amino acids 2-433 of SEQ ID NO:2 and amino acids 2-433 of SEQ ID NO:3.

Allelic variants of RUP41 GPCR are envisioned to be within the scope of the invention.

Mammalian orthologs of human RUP41 polypeptide of SEQ ID NO:2 or SEQ ID NO:3 are envisioned to be within the scope of the invention. In some embodiments, said mammalian ortholog encompasses mouse RUP41, rat RUP41, pig RUP41, and non-human primate RUP41.

Variant polypeptides at least 90%, 91%, 92%, 93%, 94%, 95%, 96%, 97%, 98% or 99% identical to RUP41 polypeptide of SEQ ID NO:2, SEQ ID NO:3, or SEQ ID NO:5 are envisioned to be within the scope of the invention. In a particularly some embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402; the disclosures of which are incorporated by reference in their entirety]. Said variant polypeptide may comprise one or more amino acid deletions, insertions, and substitutions. Variant polypeptides that are constitutively activated versions of RUP41 polypeptide of SEQ ID NO:2, SEQ ID NO:3, or SEQ ID NO:5 are envisioned to be within the scope of the invention. In some embodiments, said constitutively activated version of RUP41 polypeptide is the polypeptide of SEQ ID NO:2 or SEQ ID NO:3 wherein the phenylalanine at amino acid position 312 of SEQ ID NO:2 or SEQ ID NO:3 is substituted with lysine.

In some embodiments, said known ligand of the receptor is a modulator of the second aspect.

In some embodiments, said known ligand comprises a label selected from the group consisting of:

(a) radioisotope;
(b) enzyme; and
(c) fluorophore.

In some preferred embodiments, said label is radioisotope. In some embodiments, said radioisotope is $^3$H.

In a twenty-ninth aspect, the invention features a method of radioimaging comprising providing or administering to an individual in need of said radioimaging a radiolabeled compound, wherein said compound is selected from the group consisting of a modulator of the second aspect and a ligand of the twenty-eighth aspect.

In some embodiments, said individual is a mammal. In some embodiments, said mammal is a horse, cow, sheep, pig, cat, dog, rabbit, mouse, rat, non-human primate or human. More preferred is mouse, rat or human. Most preferred is human.

In a thirtieth aspect, the invention features a non-human mammal transgenic for a human RUP41 GPCR. In some embodiments, said non-human mammal is mouse, rat or pig.

In some embodiments, said human RUP41 GPCR comprises a polypeptide selected from the group consisting of:

(a) the polypeptide of SEQ ID NO:2;
(b) the polypeptide of SEQ ID NO:2 wherein the phenylalanine at amino acid position 312 of SEQ ID NO:2 is substituted with lysine;
(c) the polypeptide of SEQ ID NO:3; and
(d) the polypeptide of SEQ ID NO:3 wherein the phenylalanine at amino acid position 312 of SEQ ID NO:3 is substituted with lysine.

Allelic variants of RUP41 GPCR are envisioned to be within the scope of the invention.

In some embodiments, said transgenic expression of human RUP41 is cardiomyocyte selective.

In a thirty-first aspect, the invention uses the transgenic non-human mammal of the thirtieth aspect to identify whether a compound of the invention has therapeutic efficacy for cardioprotection.

In some embodiments, said non-human mammal is mouse, rat or pig.

Said compound can be assessed for therapeutic efficacy for cardioprotection by administering said compound to said transgenic non-human mammal and determining if said administration leads to a reduction in IS/AAR in the in vivo rat model of Example 18 or an in vivo model in mouse or pig analogous thereto relative to said transgenic non-human mammal administered vehicle alone.

In some embodiments, said compound can be assessed for therapeutic efficacy for cardioprotection by administering said compound to said transgenic non-human mammal and determining if said administration leads to an effect selected from the group consisting of:

(a) a decrease in cardiac hypertrophy;
(b) an increase in cardiac ejection volume;
(c) a decrease in ventricular chamber volume; and
(d) a decrease in cardiomyocyte apoptosis;

wherein a determination of said effect is indicative of the compound having said therapeutic efficacy.

In some embodiments, said compound of the invention is a modulator of the second aspect.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 μM to 100 μM. In some embodiments, said modulator has an EC50 or IC50 on human RUP41 GPCR of SEQ ID NO:2 or SEQ ID NO:3 of less than a value selected from the group consisting of 1 μM, 10 μM, 20 μM, 30 μM, 40 μM, 50 μM, 60 μM, 70 μM, 80 μM, 90 μM, and 100 μM. In some embodiments, said modulator has an EC50 or IC50 on human RUP41 GPCR of SEQ ID NO:2 or SEQ ID NO:3 of less than a value selected from the interval of 1 μM to 10 μM. In some embodiments, said modulator has an EC50 or IC50 on human RUP41 GPCR of SEQ ID NO:2 or SEQ ID NO:3 of less than a value selected from the group consisting of 1 μM, 2 μM, 3 μM, 4 μM, 5 μM, 6 μM, 7 μM, 8 μM, 9 μM, and 10 μM.

In some embodiments, said modulator lowers the level of intracellular cAMP.

In some embodiments, said modulator is selective.

In some embodiments, said modulator is orally bioavailable.

In some embodiments, said modulator is an agonist.

In some embodiments, said compound of the invention is a ligand of the thirtieth aspect.

In a thirty-second aspect, the invention features a process for making a modulator of a RUP41 GPCR, comprising the steps of:

(a) identifying said modulator according to a method of claim 1 or claim 2; and (b) synthesizing the modulator identified in (a).

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In a thirty-third aspect, the invention features a modulator according to the second aspect for use in the changing cardiovascular function.

In some embodiments, said change in cardiovascular function is selected from the group consisting of:

(a) a decrease in cardiac hypertrophy;

(b) an increase in cardiac ejection volume;

(c) a decrease in ventricular chamber volume; And (d) a decrease in cardiomyocyte apoptosis.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In a thirty-fourth aspect, the invention features a modulator of the second aspect for use in the prevention of or treatment for a cardiovascular disorder.

In some embodiments, said cardiovascular disorder is selected from the group consisting of:

(a) reduced cardiac output; and (b) increased venous pressures.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM, 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

In a thirty-fifth aspect, the invention features a modulator of the second aspect for use in the prevention of or treatment for an ischemic heart disease.

In some embodiments, said ischemic heart disease is selected from the group consisting of:

(a) myocardial infarction;

(b) post-myocardial infarction remodelling; and (c) congestive heart failure.

In some embodiments, said modulator is selected from the group consisting of agonist, partial agonist, inverse agonist and antagonist.

In some embodiments, said modulator has an EC50 or IC50 on human RUP41 GPCR of SEQ ID NO:2 or SEQ ID NO:3 of less than a value selected from the interval of 1 µM to 100 µM. In some embodiments, said modulator has an EC50 or IC50 on human RUP41 GPCR of SEQ ID NO:2 or SEQ ID NO:3 of less than a value selected from the group consisting of 1 µM, 10 µM, 20 µM, 30 µM, 40 µM, 50 µM, 60 µM, 70 µM, 80 µM, 90 µM, and 100 µM. In some embodiments, said modulator has an EC50 or IC50 on human RUP41 GPCR of SEQ ID NO:2 or SEQ ID NO:3 of less than a value selected from the interval of 1 µM to 10 µM. In some embodiments, said modulator has an EC50 or IC50 on human RUP41 GPCR of SEQ ID NO:2 or SEQ ID NO:3 of less than a value selected from the group consisting of 1 µM, 2 µM, 3 µM, 4 µM, 5 µM 6 µM, 7 µM, 8 µM, 9 µM, and 10 µM.

In some embodiments, said modulator lowers the level of intracellular cAMP.

In some embodiments, said modulator is selective.

In some embodiments, said modulator is orally bioavailable.

In some embodiments, said modulator is an agonist.

Applicant reserves the right to exclude any one or more candidate compounds from any of the embodiments of the invention. Applicant also reserves the right to exclude any one or more modulators from any of the embodiments of the invention. Applicant further reserves the right to exclude any polynucleotide or polypeptide from any of the embodiments of the invention. Applicant additionally reserves the right to exclude any ischemic heart disease or any cardiovascular disorder or any disorder of cardiomyocyte apoptosis from any of the embodiments of the invention.

BRIEF DESCRIPTION OF THE DRAWINGS

FIG. 1 depicts results from a primary screen of candidate compounds against a "target receptor" which is a Gsα Fusion Protein of an endogenous, constitutively active Gs-coupled GPCR. Results for "Compound A" are provided in well A2. Results for "Compound "B" are provided in well G9.

FIG. 10. Oligonucleosomal DNA fragmentation (aka laddering) demonstrates that reoxygenation (24 hours) following hypoxia (8 hours) stimulates increased apoptosis in NRVMs (H8/N24) infected with a control (AdGFP) adenovirus at 100 PFU/cell. However, adenovirus mediated overexpression of RUP41 (100 PFU/cell) reduces the level of DNA fragmentation induced by serum deprivation (normox) and reoxygenation following hypoxia (H8/N24).

DETAILED DESCRIPTION

Figure 1:
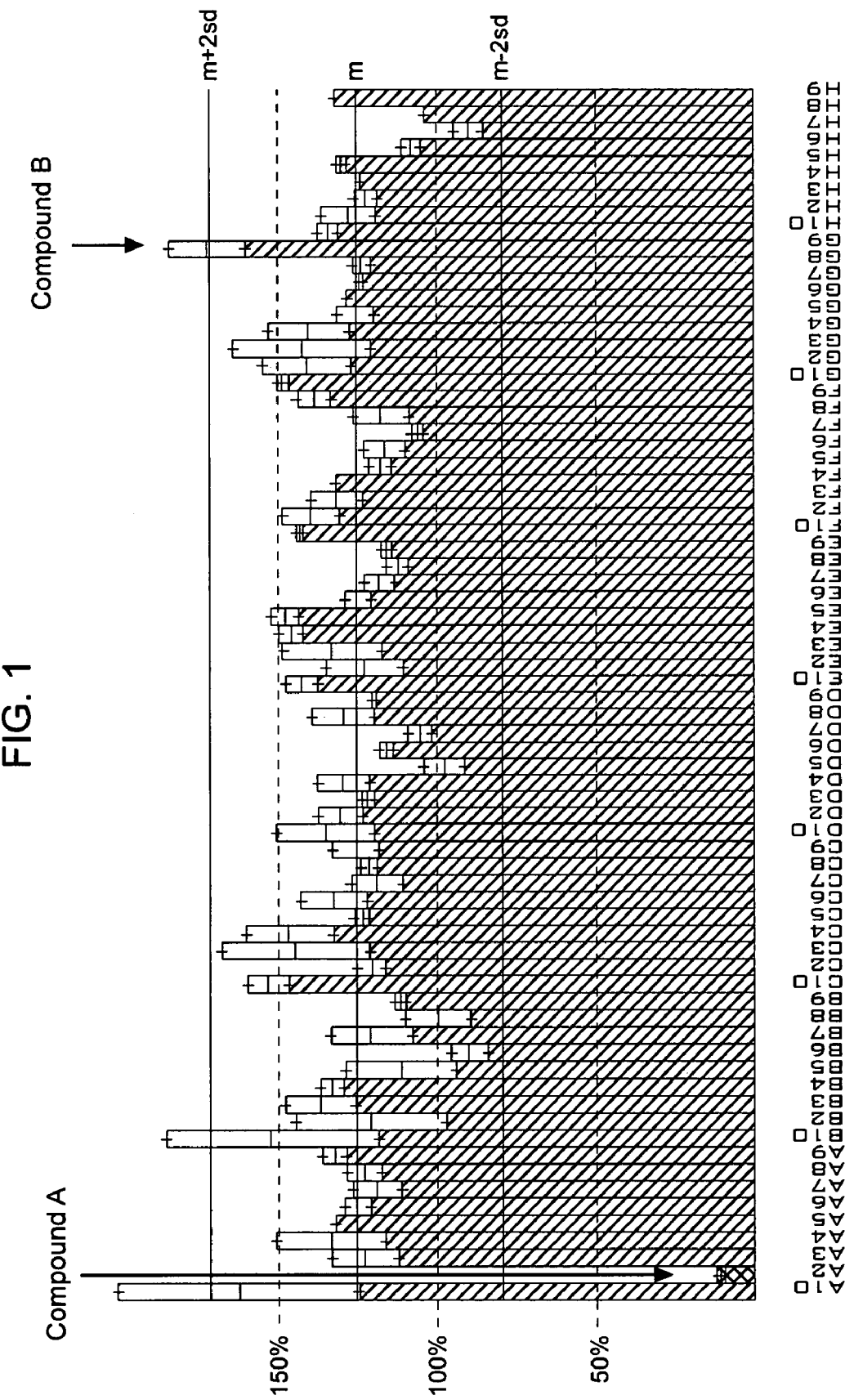
FIG. 1. By way of illustration and not limitation.

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate an intracellular response when they bind to the receptor. In some embodiments, Agonists are those materials not previously known to activate the intracellular response when they bind to the receptor (e.g. to enhance GTPγS binding to membranes or to lower intracellular cAMP level). In some embodiments, agonists are those materials not previously known to inhibit lipolysis when they bind to the receptor.

ALLOSTERIC MODULATORS shall mean materials (e.g., ligands, candidate compounds) that affect the functional activity of the receptor but which do not inhibit the endogenous ligand from binding to the receptor. Allosteric modulators include inverse agonists, partial agonists and agonists.

AMINO ACID ABBREVIATIONS used herein are set out in Table A:

TABLE A

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONISTS shall mean materials (e.g., ligands, candidate compounds) that competitively bind to the receptor at the same site as the agonists but which do not activate an intracellular response, and can thereby inhibit the intracellular responses elicited by agonists. Antagonists do not diminish the baseline intracellular response in the absence of an agonist. In some embodiments, antagonists are those materials not previously known to compete with an agonist to inhibit the cellular response when they bind to the receptor, e.g. wherein the cellular response is GTPγS binding to membranes or to the lowering of intracellular cAMP level.

ANTIBODIES are intended herein to encompass monoclonal antibodies and polyclonal antibodies. Antibodies are further intended to encompass IgG, IgA, IgD, IgE, and IgM. Antibodies include whole antibodies, including single-chain whole antibodies, and antigen binding fragments thereof, including Fab, Fab', F(ab)2 and F(ab')2. Antibodies may be from any animal origin. Preferably, antibodies are human, murine, rabbit, goat, guinea pig, hamster, camel, donkey, sheep, horse or chicken. Preferably antibodies have binding affinities with a dissociation constant or Kd value less than $5\times10^{-6}$M, $10^{-6}$M, $5\times10^{-7}$M, $10^{-7}$M, $5\times10^{-8}$M, $10^{-8}$M, $5\times10^{-9}$ M, $10^{-9}$M, $5\times10^{-10}$M $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M $10^{-14}$M, $5\times10^{-15}$M and $10^{-15}$M. Antibodies of the present invention may be prepared by any suitable method known in the art.

APOPTOSIS (also known as Programmed Cell Death) shall be taken to refer to a form of cell death wherein the cell is programmed to die by signal transduction systems that operate within the cell. In contrast, necrosis is when the cell is killed by extrinsic factors.

CANDIDATE COMPOUND shall mean a molecule (for example, and not limitation, a chemical compound) that is amenable to a screening technique. Preferably, the phrase "candidate compound" does not include compounds which were publicly known to be compounds selected from the group consisting of inverse agonist, agonist or antagonist to a receptor; more preferably, not including a compound which has previously been determined to have therapeutic efficacy in at least one mammal; and, most preferably, not including a compound which has previously been determined to have therapeutic utility in humans.

CARDIAC EJECTION FRACTION shall be taken to refer to the fraction of blood ejected from the left ventricle with a single contraction. For example, if 100 ml of blood is in the left ventricle and 90 ml is ejected upon contraction, then the cardiac ejection fraction is 90%.

CARDIAC HYPERTROPHY shall be taken to refer to enlargement of the heart muscle (myocardium). Cardiac hypertrophy is usually, but not always, an adaptive response to increased hemodynamic load imposed upon the myocardium.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

COMPOSITION means a material comprising at least one component; a "pharmaceutical composition" is an example of a composition.

COMPOUND EFFICACY shall mean a measurement of the ability of a compound to inhibit or stimulate receptor functionality; i.e. the ability to activate/inhibit a signal transduction pathway, in contrast to receptor binding affinity. Exemplary means of detecting compound efficacy are disclosed in the Example section of this patent document.

COMPRISING, CONSISTING ESSENTIALLY OF, and CONSISTING OF are defined herein according to their standard meaning. A defined meaning set forth in the M.P.E.P. controls over a defined meaning in the art and a defined meaning set forth in controlling Federal Circuit case law controls over a meaning set forth in the M.P.E.P.

CONGESTIVE HEART FAILURE (CHF) shall refer to a disorder in which the heart loses its ability to pump blood efficiently. Congestive heart failure becomes more prevalent with advancing age. Ischemic heart disease is the most common cause of congestive heart failure, accounting for 60-70% of all cases. An increased venous pressure greater than 12 mmHg is one of the major Framingham criteria for congestive heart failure, as is a reduction in cardiac output equivalent to a circulation time greater than 25 seconds.

CONSTITUTIVELY ACTIVE RECEPTOR shall mean a receptor stabilized in an active state by means other than through binding of the receptor to its ligand or a chemical equivalent thereof. A constitutively active receptor may be endogenous or non-endogenous.

CONSTITUTIVELY ACTIVATED RECEPTOR shall mean an endogenous receptor that has been modified so as to be constitutively active. CART is an acronym for Constitutively Activated Receptor Technology and when used herein prefixing a GPCR, shall be understood to identify said prefixed GPCR as a constitutively activated receptor.

CONSTITUTIVE RECEPTOR ACTIVATION shall mean activation of a receptor in the absence of binding to its ligand or a chemical equivalent thereof.

CONTACT or CONTACTING shall mean bringing at least two moieties together, whether in an in vitro system or an in vivo system.

DECREASE is used to refer to a reduction in a measurable quantity and is used synonymously with the terms "reduce", "diminish", "lower", and "lessen".

ECHOCARDIOGRAPHY shall be taken to refer to a method of using sound waves to measure cardiac structure and function in living animals.

ENDOGENOUS shall mean a material that a mammal naturally produces. Endogenous in reference to, for example and not limitation, the term "receptor," shall mean that which is naturally produced by a mammal (for example, and not limitation, a human). Endogenous shall be understood to encompass allelic variants of a gene represented within the genome of said mammal as well as the allelic polypeptide variants so encoded. By contrast, the term NON-ENDOGENOUS in this context shall mean that which is not naturally produced by a mammal (for example, and not limitation, a human). For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

EXPRESSION VECTOR is defined herein as a DNA sequence that is required for the transcription of cloned DNA and the translation of the transcribed mRNA in an appropriate host cell recombinant for said expression vector. An appropriately constructed expression vector should contain an origin of replication for autonomous replication in host cells, selectable markers, a limited number of useful restriction enzyme sites, a potential for high copy number, and active promoters. Said cloned DNA to be transcribed is operably linked to a constitutively or conditionally active promoter within said expression vector. By way of illustration and not limitation, pCMV is an expression vector.

G PROTEIN COUPLED RECEPTOR FUSION PROTEIN and GPCR FUSION PROTEIN, in the context of the invention disclosed herein, each mean a non-endogenous protein comprising an endogenous, constitutively active GPCR or a non-endogenous, constitutively activated GPCR fused to at least one G protein, most preferably the alpha (a) subunit of such G protein (this being the subunit that binds GTP), with the G protein preferably being of the same type as the G protein that naturally couples with endogenous orphan GPCRP For example, and not limitation, in an endogenous state, if the G protein "$G_s\alpha$" is the predominate G protein that couples with the GPCR, a GPCR Fusion Protein based upon the specific GPCR would be a non-endogenous protein comprising the GPCR fused to $G_s\alpha$; in some circumstances, as will be set forth below, a non-predominant G protein can be fused to the GPCR. The G protein can be fused directly to the C-terminus of the constitutively active GPCR or there may be spacers between the two.

HOST CELL shall mean a cell capable of having a vector incorporated therein. The host cell may be prokaryotic or eukaryotic. In some embodiments the host cell is eukaryotic, preferably, mammalian, and more preferably selected from the group consisting of 293, 293T, CHO and COS-7 cells. In some embodiments, the host cell is eukaryotic, more preferably melanophore.

IN NEED OF TREATMENT as used herein refers to a judgement made by a caregiver (e.g. physician, nurse, nurse practitioner, etc. in the case of humans; veterinarian in the case of animals, including non-human mammals) that an individual or animal requires or will benefit from treatment. This judgement is made based on a variety of factors that are in the realm of a caregiver's expertise, but which include the knowledge that the individual or animal is ill, or will be ill, as the result of a condition that is treatable by the compounds of the invention.

INCREASED VENOUS PRESSURE shall be taken to refer to the elevated blood pressure that develops in the venous system (veins) due to pooling of blood there caused by a weakening of the circulatory system.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean materials (e.g. ligand, candidate compound) that bind either to the endogenous form or to the constitutively activated form of the receptor so as to reduce the baseline intracellular response of the receptor observed in the absence of agonists.

ISCHEMIC HEART DISEASE shall refer to a disorder caused by lack of oxygen to the tissues of the heart, in which muscles of the heart are affected and the heart cannot pump properly. Ischemic heart disease is the most common cardiomyopathy in the United States.

ISOLATED shall mean that the material is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such a polynucleotide could be part of a vector and/or such a polynucleotide or polypeptide could be part of a composition, and still be isolated in that the vector or composition is not part of its natural environment.

KNOCKOUT MOUSE/RAT is intended herein to encompass a mouse or rat that has been manipulated by recombinant means such that a single gene of choice has been inactivated or "knocked-out" in a manner that leaves all other genes unaffected.

KNOWN RECEPTOR shall mean an endogenous receptor for which the endogenous ligand specific for that receptor has been identified.

LIGAND shall mean a molecule specific for a naturally occurring receptor.

As used herein, the terms MODULATE or MODIFY are meant to refer to an increase or decrease in the amount, quality, or effect of a particular activity, function or molecule.

MYOCARDIAL INFARCTION shall refer to the damage or death of an area of heart muscle because of an inadequate supply of oxygen to that area. Myocardial infarctions are often caused by a clot that blocks one of the coronary arteries (the blood vessels that bring blood and oxygen to heart muscle). The clot prevents blood and oxygen from reaching that area of the heart, leading to the death of heart cells in that area.

NON-ORPHAN RECEPTOR shall mean an endogenous naturally occurring molecule specific for an identified ligand wherein the binding of a ligand to a receptor activates an intracellular signaling pathway.

ORPHAN RECEPTOR shall mean an endogenous receptor for which the ligand specific for that receptor has not been identified or is not known.

PARTIAL AGONISTS shall mean materials (e.g., ligands, candidate compounds) that activate the intracellular response when they bind to the receptor to a lesser degree/extent than do full agonists.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

POLYNUCLEOTIDES shall mean RNA, DNA, or RNA/DNA hybrid sequences of more than one nucleotide in either single chain or duplex form. The polynucleotides of the invention may be prepared by any known method, including synthetic, recombinant, er vivo generation, or a combination thereof, as well as utilizing any purification methods known in the art.

POLYPEPTIDE shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

POST-MYOCARDIAL INFARCTION REMODELING. The loss of myocardial tissue due to myocardial infarction results in a sustained excessive hemodynamic burden placed on the ventricle. Ventricular hypertrophy constitutes one of the principle mechanisms by which the heart compensates for an increased load. However, the capacity for this adaptation to sustain cardiac performance in the face of hemodynamic overload is finite and, when chronically maintained, becomes maladaptive. Gradually, the adaptive hypertrophic phenotype transitions to overt heart failure as the enlarged ventricles progressively diltate and contractile function weakens. The natural history of the adaptive and maladaptive response to myocardial infarction in the heart is referred to as 'remodeling'.

With regard to post-myocardial infarction remodeling, there are a number of parameters that are informative with regard to the progression of the pathology:

(a) if cardiac hypertrophy increases, that is detrimental;

(b) if cardiac myocyte apoptosis increases, that is detrimental;

(c) if cardiac ejection fraction decreases, that is detrimental; and (d) if ventricular chamber volume increases, that is detrimental.

Measuring ejection fraction, hypertrophy, and chamber dilation can all be done in living animals with echocardiography, including in rats and mice. These parameters are typically looked at initially. In order to accurately ascertain the pathogenetic mechanisms involved, however, the animal typically further needs to be sacrificed in order to measure cardiomyocyte apoptosis.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins.

REDUCED CARDIAC OUTPUT shall be taken to refer to the decreased pumping capacity of the failing heart such that less blood is pumped into the circulatory system (arteries) with each contraction of the heart's ventricles.

SECOND MESSENGER shall mean an intracellular response produced as a result of receptor activation. A second messenger can include, for example, inositol triphosphate ($IP_3$), diacylglycerol (DAG), cyclic AMP (cAMP), cyclic GMP (cGMP), and $Ca^{2+}$. Second messenger response can be measured for a determination of receptor activation. In addition, second messenger response can be measured for the direct identification of candidate compounds, including for example, inverse agonists, partial agonists, agonists, and antagonists.

SIGNAL TO NOISE RATIO shall mean the signal generated in response to activation, amplification, or stimulation wherein the signal is above the background noise or the basal level in response to non-activation, non-amplification, or non-stimulation.

SPACER shall mean a translated number of amino acids that are located after the last codon or last amino acid of a gene, for example a GPCR of interest, but before the start codon or beginning regions of the G protein of interest, wherein the translated number amino acids are placed in-frame with the beginnings regions of the G protein of interest. The number of translated amino acids can be one, two, three, four, etc., and up to twelve.

STIMULATE or STIMULATING, in relationship to the term "response" shall mean that a response is increased in the presence of a compound as opposed to in the absence of the compound SUBJECT shall mean primates, including but not limited to humans and baboons, as well as pet animals such as dogs and cats, laboratory animals such as rats and mice, and farm animals such as horses, sheep, and cows.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

TRANSGENIC MOUSE/RAT shall be intended herein to encompass a mouse or rat that has been engineered through recombinant means to carry a foreign gene, or transgene, of choice as part of its own genetic material.

VENTRICULAR CHAMBER VOLUME shall be taken to refer to a measurement of the internal dimensions of the left or right ventricular chambers of the heart. In the failing heart, there is an enlargement of the ventricular chambers.

A. Introduction

The order of the following sections is set forth for presentational efficiency and is not intended, nor should be construed, as a limitation on the disclosure or the claims to follow.

B. Screening of Candidate Compounds

1. Generic GPCR Screening Assay Techniques

When a G protein receptor becomes active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid PIP$_2$, releasing two intracellular messengers: diacyclglycerol (DAG) and inistol 1,4,5-triphoisphate (IP$_3$). Increased accumulation of IP$_3$ is associated with activation of Gq- and Go-associated receptors. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Assays that detect IP$_3$ accumulation can be utilized to determine if a candidate compound is, e.g., an inverse agonist to a Gq- or Go-associated receptor (i.e., such a compound would decrease the levels of IP$_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR Coupling of the G protein to the GPCR provides a signaling pathway that can be assessed. In some embodiments it is preferred that screening take place using a mammalian expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR. In some embodiments, the GPCR Fusion Protein is preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments it is preferred, that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 5(a) below) be available for insertion of an endogenous GPCR sequence therein; this provides for further efficiency in the context of large-scale screening of a variety of different endogenous GPCRs having different sequences.

As noted above, activated GPCRs that couple to Gi, Gz and Go are expected to inhibit the formation of cAMP making assays based upon these types of GPCRs challenging [i.e., the cAMP signal decreases upon activation, thus making the direct identification of, e.g., agonists (which would further decrease this signal) challenging]. As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE B

| G protein | Effect of cAMP Production upon Activation of GPCR (i.e., constitutive activation or agonist binding) | Effect of IP$_3$ Accumulation upon Activation of GPCR (i.e., constitutive activation or agonist binding) | Effect of cAMP Production upon contact with an Inverse Agonist | Effect on IP$_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will forces the endogenous Gi coupled receptor to couple to its non-endogenous G protein, Gq, such that the second messenger, for example, inositol triphosphate or diacylglycerol, can be measured in lieu of cAMP production.

4. Co-Transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In some embodiments, an effective technique in measuring the decrease in production of cAMP as an indication of activation of a receptor that predominantly couples Gi upon activation can be accomplished by co-transfecting a signal enhancer, e.g., a non-endogenous, constitutively activated receptor that predominantly couples with Gs upon activation (e.g., TSHR-A623I; see infra), with the Gi linked GPCRP As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

C. Medicinal Chemistry

Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation-based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of individual members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Candidate Compounds Identified as Modulators

Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

In some embodiments, said identified modulator is bioavailable. A number of computational approaches available to those of ordinary skill in the art have been developed for prediction of oral bioavailability of a drug [Ooms et al., Biochim Biophys Acta (2002) 1587:118-25; Clark & Grootenhuis, Curr OpinDrug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is hereby incorporated by reference in its entirety). Furthermore, positron emission tomography (PET) has been successfully used by a number of groups to obtain direct measurements of drug distribution, including an assessment of oral bioavailability, in the mammalian body following oral administration of the drug, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is hereby incorporated by reference in its entirety]. Also, see infra, including Example 19.

D. Pharmaceutical Compositions

The invention provides methods of treatment (and prevention) by administration to an individual in need of said treatment (or prevention) a therapeutically effect amount of a modulator of the invention [also see, e.g., PCT Application Number PCT/IB02/01461 published as WO 02/066505 on 29 Aug. 2002; the disclosure of which is hereby incorporated by reference in its entirety]. In a preferred aspect, the modulator is purified. The individual is preferably an animal including, but not limited to animals such as cows, pigs, horses, chickens, cats, dogs, rabbits, rats, mice, etc., and is preferably a mammal, and most preferably human.

Modulators of the invention can be administered to non-human animals [see Examples, infra] and/or humans, alone or in pharmaceutical or physiologically acceptable compositions where they are mixed with suitable carriers or excipient(s) using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

The pharmaceutical or physiologically acceptable composition is then provided at therapeutically effect dose. A therapeutically effective dose refers to that amount of a modulator sufficient to result in prevention or amelioration of symptoms or physiological status of an ischemic heart disease, including myocardial infarction, post-myocardial infarction remodeling, and congestive heart failure as determined illustratively and not by limitation by the methods described herein. In some embodiments, a therapeutically effective dose refers to that amount of a modulator sufficient to result in prevention or amelioration of symptoms or physiological status of a cardiovascular disorder, including reduced cardiac output and increased venous pressures as determined illustratively and not by limitation by the methods described herein. In some embodiments, a therapeutically effective dose refers to that amount of a modulator sufficient to effect a needed change in cardiovascular function, including a decrease in cardiac hypertrophy, an increase in cardiac ejection volume, a decrease in ventricular chamber volume, and a decrease in cardiomyocyte apoptosis as determined illustratively and not by limitation by the methods described herein.

It is expressly considered that the modulators of the invention may be provided alone or in combination with other pharmaceutically or physiologically acceptable compounds. Other compounds for the treatment of disorders of the invention are currently well known in the art. One aspect of the invention encompasses the use according to embodiments disclosed herein further comprising one or more agents selected from the group consisting of captopril, enalapril maleate, lininopril, ramipril, perindopril, furosemide, torasemide, chlorothiazide, hydrochlorothiazide, amiloride hydrochloride, spironolactone, atenolol, bisoprolol, carvedilol, metoprolol tartrate, and digoxin.

In some embodiments the ischemic heart disease is selected from the group consisting of myocardial infarction, post-myocardial infarction remodeling, and congestive heart failure. In some embodiments, the cardiovascular disorder is selected from the group consisting of reduced cardiac output and increased venous pressures. In some embodiments, the needed change in cardiovascular function is selected from the group consisting of a decrease in cardiac hypertrophy, an increase in cardiac ejection volume, a decrease in ventricular chamber volume, and a decrease in cardiomyocyte apoptosis.

Routes of Administration

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated. In some embodiments, route of administration is oral.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carrier and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in multi-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a particular embodiment, the compounds can be delivered via a controlled release system. In one embodiment, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321: 574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, N.Y., 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). Other controlled release systems are discussed in the review by Langer (1990, Science 249:1527-1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to cell death-protective in an in vitro system. [See Examples, infra, for in vitro assays and in vivo animal models.] Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the test population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to prevent or treat a disorder of the invention, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10-90% of the time, preferably between 30-99%, and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results, including but not limited to prevention or treatment of an ischemic heart disease of the invention, prevention or treatment of a cardiovascular disorder of the invention, or the effecting of a needed change in cardiovascular function of the invention, is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Of course, these daily dosages can be delivered or administered in small amounts periodically during the course of a day. It is noted that these dosage ranges are only preferred ranges and are not meant to be limiting to the invention.

E. Methods of Treatment

The invention is drawn inter alia to methods of preventing or treating an ischemic heart disease, including myocardial infarction, post-myocardial infarction remodeling, and congestive heart failure, comprising providing an individual in need of such treatment with a modulator of the invention. The invention is also drawn inter alia to methods of preventing or treating a cardiovascular disorder, including reduced cardiac output and increased venous pressures, comprising providing an individual in need of such treatment with a modulator of the invention. The invention is also drawn inter alia to methods of effecting a needed change in cardiovascular function, including a decrease in cardiac hypertrophy, an increase in cardiac ejection volume, a decrease in ventricular chamber volume, and a decrease in cardiomyocyte apoptosis, comprising providing an individual in need of such treatment with a modulator of the invention. In some embodiments, said modulator is orally bioavailable. In some embodiments, the modulator is provided to the individual in a pharmaceutical composition that is taken orally. Preferably the individual is a mammal, and most preferably a human.

F. Other Utility

Agents that modulate (i.e., increase, decrease, or block) cardiomyocyte-protective RUP41 receptor functionality may be identified by contacting a candidate compound with RUP41 receptor and determining the effect of the candidate compound on RUP41 receptor functionality. The selectivity of a compound that modulates the functionality of RUP41 receptor can be evaluated by comparing its effects on RUP41 receptor to its effects on other receptors. Following identification of compounds that modulate RUP41 receptor functionality, such candidate compounds may be further tested in other assays including, but not limited to, in vivo models, in order to confirm or quantitate their activity. Modulators of RUP41 receptor functionality will be therapeutically useful in treatment of diseases and physiological conditions in which normal or aberrant RUP41 receptor functionality is involved.

Agents that are modulators (i.e., increase, decrease, or block) of cardioprotection may be identified by contacting a candidate compound with a RUP41 receptor and determining the effect of the candidate compound on RUP41 receptor functionality. In some embodiments, said cardioprotection comprises prevention or reduction of cardiomyocyte death. In some embodiments, said cardiomyocyte death comprises cardiomyocyte apoptosis. In some embodiments, said cardioprotection comprises myocardial protection against ischemia. In some embodiments, said cardioprotection comprises reduced size of infarction. In some embodiments, said cardioprotection comprises improved postischemic contractile recovery. In some embodiments, said cardioprotection comprises suppression of malignant ischemia-induced arrhythmias. The selectivity of a compound that modulates the functionality of RUP41 receptor can be evaluated by comparing its effects on RUP41 receptor to its effects on other receptors. Following identification of compounds that modulate RUP41 receptor functionality, such candidate compounds may be further tested in other assays including, but not limited to, in vivo models, in order to confirm or quantitate their activity. Modulators of RUP41 receptor functionality will be therapeutically useful in treatment of diseases and physiological conditions in which normal or aberrant RUP41 functionality is involved.

The present invention also relates to radioisotope-labeled versions of compounds of the invention identified as modulators or ligands of RUP41 that would be useful not only in radio-imaging [see, e.g., Lemstra et al., Gerontology (2003) 49:55-60; Myers et al., J Psychopharmacol (1999) 13:352-7; the disclosures of which are hereby incorporated by reference in their entireties] but also in assays, both in vitro and in vivo, for localizing and quantitating RUP41 in tissue samples, including human, and for identifying RUP41 ligands by inhibition binding of a radioisotope-labeled compound. It is a further object of this invention to develop novel RUP41 assays of which comprise such radioisotope-labeled compounds. By way of illustration and not limitation, it is envisioned that visualization of RUP41 through radio-imaging may identify an individual at risk for or progressing toward ischemic heart disease, including myocardial infarction, post-myocardial infarction remodeling, and congestive heart failure.

The present invention embraces radioisotope-labeled versions of compounds of the invention identified as modulators or ligands of RUP41.

In some embodiments, a radioisotope-labeled version of a compound is identical to the compound, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (deuterium), $^3H$ (tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compound will depend on the specific application of that radio-labeled compound. For example, for in vitro RUP41 labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful. In some embodiments, the radionuclide is selected from the group consisting of $^3H$, $^{11}C$, $^{18}F$, $^{14}C$, $^{125}I$, $^{124}I$, $^{131}I$, 35S and $^{82}Br$.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3H$]—This procedure is rather inexpensive and requires precursors containing reducible functional groups such as aldehydes, ketones, lactones, esters, and the like.

C. Reduction with Lithium Aluminum Hydride [$^3H$]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3H$]—This procedure is usually employed to prepare O-methyl or N-methyl ($^3H$) products by treating appropriate precursors with high specific activity methyl iodide ($^3H$). This method in general allows for higher specific activity, such as for example, about 70-90 Ci/mmol.

Synthetic methods for incorporating activity levels of $^{125}I$ into target molecules include:

A. Sandmeyer and like reactions—This procedure transforms an aryl or heteroaryl amine into a diazonium salt, such as a tetrafluoroborate salt, and subsequently to $^{125}I$ labeled compound using Na $^{125}I$. A represented procedure was reported by Zhu, D.-G. and co-workers in *J. Org. Chem.* 2002, 67, 943-948.

B. Ortho $^{125}I$odination of phenols—This procedure allows for the incorporation of $^{125}I$ at the ortho position of a phenol as reported by Collier, T. L. and co-workers in *J. Labeled Compd Radiopharm.* 1999, 42, S264S266.

C. Aryl and heteroaryl bromide exchange with $^{125}I$—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

In some embodiments, a radioisotope-labeled version of a compound is identical to the compound, but for the addition of one or more substituents comprising a radionuclide. In some further embodiments, the compound is a polypeptide. In some further embodiments, the compound is an antibody or an antigen-binding fragment thereof. In some further embodiments, said antibody is monoclonal. Suitable said radionuclide includes but is not limited to $^2H$ (deuterium), $^3H$ (tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compound will depend on the specific application of that radiolabeled compound. For example, for in vitro RUP41 labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Methods for adding one or more substituents comprising a radionuclide are within the purview of the skilled artisan and include, but are not limited to, addition of radioisotopic iodine by enzymatic method [Marchalonic J J, Biochemical Journal (1969) 113:299-305; Thorell J I and Johansson B G, Biochimica et Biophysica Acta (1969) 251:363-9; the disclosure of each of which is hereby incorporated by reference in its entirety] and or by Chloramine-T/Iodogen/Iodobead methods [Hunter W M and Greenwood F C, Nature (1962) 194: 495-6; Greenwood F C et al., Biochemical Journal (1963) 89:114-23; the disclosure of each of which is hereby incorporated by reference in its entirety].

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. The mutational approach disclosed herein does not rely upon this approach but is instead based upon an algorithmic approach and a positional distance from a conserved proline residue located within the TM6 region of human GPCRs. Once this approach is secured, those in the art are credited with the ability to make minor modifications thereto to achieve substantially the same results (i.e., constitutive activation) disclosed herein. Such modified approaches are considered within the purview of this disclosure.

The following Examples are provided for illustrative purposes and not as a means of limitation. One of ordinary skill in the art would be able to design equivalent assays and methods based on the disclosure herein, all of which form part of the present invention.

Although a variety of expression vectors are available to those in the art, for purposes of utilization for both the endogenous and non-endogenous GPCRs, in some embodiments it is preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. In some embodiments it is preferred that the vector utilized be an adenoviral expression vector.

Recombinant DNA techniques relating to the subject matter of the present invention and well known to those of ordinary skill in the art can be found, e.g., in Maniatis T et al., *Molecular Cloning: A Laboratory Manual* (1989) Cold Spring Harbor Laboratory; U.S. Pat. No. 6,399,373; and PCT Application Number PCT/IB02/01461 published as WO 02/066505 on 29 Aug. 2002; the disclosure of each of which is hereby incorporated by reference in its entirety.

Example 1

Full-Length Cloning of Endogenous Human RUP41

The disclosed human RUP41 was identified based upon the use of the GenBank database information. While searching the database, a cDNA clone with Accession Number U66581 was identified as a human genomic sequence from chromosome 7. The full length RUP41 was cloned by PCR using primers:

5'-TCCCCCGGGAAAAAAACCAACTGCTCCAAA-3' (SEQ ID NO:7; sense),

5'-TAGGATCCATTTGAATGTGGATTTGGTGAAA-3' (SEQ ID NO:8; antisense, containing a BamHI site)

and human genomic DNA as template. Amplification was carried out using rTth polymerase (Perkin Elmer) with the buffer system provided by the manufacturer, 0.25 mM of each primer, and 0.2 mM of each 4 nucleotides. The cycle condition was 30 cycles of 94° C. for 1 min, 50° C. for 1 min and 72° C. for 1.5 min. The 5' PCR primer was kinased and the 1.38 kb PCR fragment was digested with BamHI and cloned into EcoRV-BamHI site of pCMV expression vector. See, SEQ ID NO:1 for nucleic acid sequence and SEQ ID NO:2 for deduced amino acid sequence.

Example 2

Preparation of Non-Endogenous, Constitutively Activated Human RUP41

Those skilled in the art are credited with the ability to select techniques for mutation of a nucleic acid sequence. Presented below are approaches utilized to create non-endogenous versions of human GPCRs. The mutation disclosed below for RUP41 is based upon an algorithmic approach whereby the 16$^{th}$ amino acid (located in the IC3 region of the GPCR) from a conserved proline (or an endogenous, conservative substitution therefor) residue (located in the TM6 region of the GPCR, near the TM6/IC3 interface) is mutated, preferably to an alanine, histidine, arginine or lysine amino acid residue, most preferably to a lysine amino acid residue.

Non-endogenous, constitutively activated full-length human RUP41 is accomplished by mutation of the phenylalanine residue at amino acid position 312 of SEQ ID NO:2 or SEQ ID NO:3 to lysine (F312K).

1. Transformer Site-Directed™ Mutagenesis

Preparation of non-endogenous human GPCRs may be accomplished on human GPCRs using, inter alia, Transformer Site-Directed™ Mutagenesis Kit (Clontech) according to the manufacturer instructions. Two mutagenesis primers are utilized, most preferably a lysine mutagenesis oligonucleotide that creates the lysine mutation, and a selection marker oligonucleotide. For convenience, the codon mutation to be incorporated into the human GPCR is also noted, in standard form.

2. QuikChange™ Site-Directed™ Mutagenesis

Preparation of non-endogenous human GPCRs can also be accomplished by using QuikChang™ Site-Directed™ Mutagenesis Kit (Stratagene, according to manufacturer's instructions). Endogenous GPCR is preferably used as a template and two mutagenesis primers utilized, as well as, most preferably, a lysine mutagenesis oligonucleotide and a selection marker oligonucleotide (included in kit). For convenience, the codon mutation incorporated into the novel human GPCR and the respective oligonucleotides are noted, in standard form.

Example 3

Receptor Expression

Although a variety of cells are available to the art for the expression of proteins, it is most preferred that mammalian cells or melanophores be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells or melanophores. Of the mammalian cells, CHO, COS-7, 293 and 293T cells are particularly preferred, although the specific mammalian cell utilized can be predicated upon the particular needs of the artisan. See infra as relates to melanophores, including Example 8.

a. Transient Transfection

On day one, $6 \times 10^6/10$ cm dish of 293 cells well are plated out. On day two, two reaction tubes are prepared (the proportions to follow for each tube are per plate): tube A is prepared by mixing 4 µg DNA (e.g., pCMV vector; pCMV vector with receptor cDNA, etc.) in 0.5 ml serum free DMEM (Gibco BRL); tube B is prepared by mixing 24 µl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA. The 12 µg of DNA is combined with 60 µl of lipofectamine and 2 mL of DME High Glucose Medium without serum. The medium is aspirated from the plates and the cells are washed once with medium without serum. The DNA, lipofectamine, and medium mixture are added to the plate along with 10 mL of medium without serum. Following incubation at 37 degrees Celsius for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/mL. The transfected cells now undergo selection for positively transfected cells containing the G418 resistant gene. The medium is replaced every four to five days as selection occurs. During selection, cells are grown to create stable pools, or split for stable clonal selection.

Example 4

Assays for Determination of GPCR Activation

A variety of approaches are available for assessment of activitation of human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to endogenous GPCRs and non-endogenous, constitutively activated GPCRs. The assay is generic and has application to drug discovery at all G protein-coupled receptors.

The [$^{35}$S]GTPγS assay is incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 µg membrane protein (this amount can be adjusted for optimization) and 10 µM GDP (this amount can be changed for optimization) for 1 hour. Wheatgerm agglutinin beads (25 µl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are then counted using a hemocytometer and additional PBS is added to give the appropriate number of cells (with a final volume of about 50 μl/well).

cAMP standards and Detection Buffer [comprising 1 μCi of tracer $^{125}$I cAMP (50 μl) to 11 ml Detection Buffer] is prepared and maintained in accordance with the manufacturer's instructions. Assay Buffer is prepared fresh for screening and contained 50 μl of Stimulation Buffer, 3 ul of test compound (12 μM final assay concentration) and 50 μl cells, Assay Buffer is stored on ice until utilized. The assay is initiated by addition of 50 μl of cAMP standards to appropriate wells followed by addition of 50 ul of PBSA to wells H-11 and H12. 50 μl of Stimulation Buffer is added to all wells. DMSO (or selected candidate compounds) was added to appropriate wells using a pin tool capable of dispensing 3 μl of compound solution, with a final assay concentration of 12 μM test compound and 100 μl total assay volume. The cells are then added to the wells and incubated for 60 min at room temperature. 100 μl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which was contained within each assay plate.

3. Cell-Based cAMP for Gi Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of constitutive activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi linked target GPCR to establish a baseline level of cAMP. Upon creating a non-endogenous version of the Gi coupled receptor, this non-endogenous version of the target GPCR is then co-transfected with the signal enhancer, and it is this material that can be used for screening. We will utilize such approach to effectively generate a signal when a cAMP assay is used; this approach is preferably used in the direct identification of candidate compounds against Gi coupled receptors. It is noted that for a Gi coupled GPCR, when this approach is used, an inverse agonist of the target GPCR will increase the cAMP signal and an agonist will decrease the cAMP signal.

On day one, $2 \times 10^4$ 293 cells/well will be plated out. On day two, two reaction tubes will be prepared (the proportions to follow for each tube are per plate): tube A will be prepared by mixing 2 μg DNA of each receptor transfected into the mammalian cells, for a total of 4 μg DNA [e.g., pCMV vector; pCMV vector with mutated THSR (TSHR-A623I); TSHR-A623I and GPCR, etc.] in 1.2 ml serum free DMEM (Irvine Scientific, Irvine, Calif.); tube B will be prepared by mixing 120 μl lipofectamine (Gibco BRL) in 1.2 ml serum free DMEM. Tubes A and B will then be admixed by inversions (several times), followed by incubation at room temperature for 30-45 min. The admixture is referred to as the "transfection mixture". Plated 293 cells will be washed with 1×PBS, followed by addition of 10 ml serum free DMEM. 2.4 ml of the transfection mixture will then be added to the cells, followed by incubation for 4 hrs at 37° C./5% CO$_2$. The transfection mixture will then be removed by aspiration, followed by the addition of 25 ml of DMEM/10% Fetal Bovine Serum. Cells will then be incubated at 37° C./5% CO$_2$. After 24 hr incubation, cells will then be harvested and utilized for analysis.

A Flash Plate™ Adenylyl Cyclase kit (New England Nuclear; Cat. No. SMP004A) is designed for cell-based assays, however, can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty four hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50 μl/well).

cAMP standards and Detection Buffer (comprising 1 μCi of tracer [$^{125}$I cAMP (50 μl] to 11 ml Detection Buffer) will be prepared and maintained in accordance with the manufacturer's instructions. Assay Buffer should be prepared fresh for screening and contained 50 μl of Stimulation Buffer, 3 μl of test compound (12 μM final assay concentration) and 50 μl cells, Assay Buffer can be stored on ice until utilized. The assay can be initiated by addition of 50 μl of cAMP standards to appropriate wells followed by addition of 50 μl of PBSA to wells H-11 and H12. Fifty μl of Stimulation Buffer will be added to all wells. Selected compounds (e.g., TSH) will be added to appropriate wells using a pin tool capable of dispensing 3 μl of compound solution, with a final assay concentration of 12 μM test compound and 100 μl total assay volume. The cells will then be added to the wells and incubated for 60 min at room temperature. 100 μl of Detection Mix containing tracer cAMP will then be added to the wells. Plates were then incubated additional 2 hours followed by counting in a Wallac MicroBeta scintillation counter. Values of cAMP/well will then be extrapolated from a standard cAMP curve which is contained within each assay plate.

4. Reporter-Based Assays a. CRE-Luc Reporter Assay (Gs-Associated Receptors)

293 and 293T cells are plated-out on 96 well plates at a density of $2 \times 10^4$ cells per well and were transfected using Lipofectamine Reagent (BRL) the following day according to manufacturer instructions. A DNA/lipid mixture is prepared for each 6-well transfection as follows: 260 ng of plasmid DNA in 100 μl of DMEM were gently mixed with 2 μl of lipid in 100 μl of DMEM (the 260 ng of plasmid DNA consisted of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see, 7 *Human Gene Therapy* 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture was added to each well. 100 µl of DMEM with 10% FCS are added to each well after a 4 hr incubation in a cell culture incubator. The following day the transfected cells are changed with 200 µl/well of DMEM with 10% FCS. Eight (8) hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue # 219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP.

c. SRF-Luc Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with 1 µM Angiotensin, where indicated: Cells are then lysed and assayed for luciferase activity using a Luclite™ Kit (Packard, Cat. # 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.)

Intracellular $IP_3$ Accumulation Assay ($G_q$-Associated Receptors)

On day 1, cells comprising the receptors (endogenous and/or non-endogenous) can be plated onto 24 well plates, usually 1×10⁵ cells/well (although his umber can be optimized. On day 2 cells can be transfected by firstly mixing 0.25 µg DNA in 50 µl serum free DMEM/well and 2 µl lipofectamine in 50 µl serumfree DMEM/well. The solutions are gently mixed and incubated for 15-30 min at room temperature. Cells are washed with 0.5 ml PBS and 400 µl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with ³H-myo-inositol. Briefly, the media is removed and the cells are washed with 0.5 ml PBS. Then 0.5 ml inositol-free/serum free media (GIBCO BRL) is added/well with 0.25 µCi of ³H-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 µM pargyline 10 mM lithium chloride or 0.4 ml of assay medium and 50 µl of 10× ketanserin (ket) to final concentration of 10 µM. The cells are then incubated for 30 min at 37° C. The cells are then washed with 0.5 ml PBS and 200 µl of fresh/ice cold stop solution (1M KOH; 18 mM Na-borate; 3.8 mM EDTA) is added/well. The solution is kept on ice for 5-10 min or until cells were lysed and then neutralized by 200 µl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol tris phosphates are eluted in scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 5

Fusion Protein Preparation a. GPCR:Gs Fusion Construct

The design of the constitutively active GPCR-G protein fusion construct was accomplished as follows: both the 5' and 3' ends of the rat G protein Gsα (long form; Itoh, H. et al., 83 PNAS 3776 (1986)) were engineered to include a HindIII (5'-AAGCTT-3') sequence thereon. Following confirmation of the correct sequence (including the flanking HindIII sequences), the entire sequence was shuttled into pcDNA3.1 (−) (Invitrogen, cat. no. V795-20) by subcloning using the HindIII restriction site of that vector. The correct orientation for the $G_s\alpha$ sequence was determined after subcloning into pcDNA3.1(−). The modified pcDNA3.1(−) containing the rat $G_s\alpha$ gene at HindIII sequence was then verified; this vector was now available as a "universal" $G_s\alpha$ protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 Amino Acid Deletion)/Gi Fusion Construct

The design of a Gq(del)/Gi fusion construct can be accomplished as follows: the N-terminal six (6) amino acids (amino acids 2 through 7, having the sequence of TLESIM $G_\alpha q$-subunit will be deleted and the C-terminal five (5) amino acids, having the sequence EYNLV will be replaced with the corresponding amino acids of the $G_\alpha i$ Protein, having the sequence DCGLF. This fusion construct will be obtained by PCR using the following primers:

(SEQ ID NO:9)
5'-gatcAAGCTTCCATGGCGTGCTGCCTGAGCGAGGAG-3'
and (SEQ ID NO:10)
5'-gatcGGATCCTTAGAACAGGCCGCAGTCCTTCAGGTTCAGCTGCAGG
ATGGTG-3' and Plasmid 63313 which contains the mouse $G_\alpha q$-wild type version with a hemagglutinin tag as template. Nucleotides in lower caps are included as spacers.

TaqPlus Precision DNA polymerase (Stratagene) will be utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product will be cloned into a pCRII-TOPO vector (Invitrogen) and sequenced using the ABI Big Dye Terminator kit (P.E. Biosystems). Inserts from a TOPO clone containing the sequence of the fusion construct will be shuttled into the expression vector pcDNA3.1(+) at the HindIII/BamHI site by a 2 step cloning process. Also see, PCT Application Number PCT/US02/05625 published as WO02068600 on 6 Sep. 2002, the disclosure of which is hereby incorporated by reference in its entirety.

Example 6

Protocol: Direct Identification of Inverse Agonists and Agonists

A. [$^{35}$S]GTPγS Assay

In some embodiments, an endogenous GPCR is utilized for the direct identification of candidate compounds as, e.g., agonists or antagonists. In some embodiments, an endogenous constitutively active GPCR or a non-endogenous constitutively activated GPCR is utilized for the direct identification of candidate compounds as, e.g., inverse agonists or agonists. In some embodiments, a GPCR Fusion Protein comprising an endogenous, constitutively active GPCR or a non-endogenous constitutively activated GPCR is utilized for the direct identification of candidate compounds as, e.g., inverse agonists. In said embodiments, the following assay protocols are provided for said direct identification.

Membrane Preparation

In some embodiments membranes comprising the GPCR/Fusion Protein of interest and for use in the direct identification of candidate compounds as, e.g., inverse agonists, agonists, or antagonists, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension.). This is referred to herein as "Membrane Protein".

Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it was noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 μl Binding Buffer. Thereafter, 10 μl of Bradford Protein Standard (1 mg/ml) will be added to each tube, and 10 μl of membrane Protein will then be added to just one tube (not the blank). Thereafter, 200 μl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

Direct Identification Assay a. Materials

GDP Buffer consisted of 37.5 ml Binding Buffer and 2 mg GDP (Sigma, cat. no. G-7127), followed by a series of dilutions in Binding Buffer to obtain 0.2 μM GDP (final concentration of GDP in each well was 0.1 μM GDP); each well comprising a candidate compound, has a final volume of 200 μl consisting of 100 μl GDP Buffer (final concentration, 0.1 μM GDP), 50 μl Membrane Protein in Binding Buffer, and 50 μl [$^{35}$S]GTpγS (0.6 nM) in Binding Buffer (2.5 μl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the GPCR Fusion Protein, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 μg/well). Thereafter, 100 μl GDP Buffer was added to each well of a Wallac Scintistrip™ (Wallac). A 5 ul pin-tool will then be used to transfer 5 μl of a candidate compound into such well (i.e., 5 μl in total assay volume of 200 μl is a 1:40 ratio such that the final screening concentration of the candidate compound is 10 μM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 μl of Membrane Protein will be added to each well (a control well comprising membranes without the GPCR Fusion Protein was also utilized), and pre-incubated for 5-10 minutes at room temperature. Thereafter, 50 μl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer instructions).

B. Cyclic AMP Assay

Another assay approach for directly identifying candidate compounds as, e.g., inverse agonists, agonists, or antagonists, is accomplished by utilizing a cyclase-based assay. In addition to direct identification, this assay approach can be utilized as an independent approach to provide confirmation of the results from the [$^{35}$S]GTPγS approach as set forth above.

A modified Flash Plate™ Adenylyl Cyclase kit (New England Nuclear; Cat. No. SMP004A) is preferably utilized for direct identification of candidate compounds as inverse agonists and agonists to endogenous or constitutively active GPCRs in accordance with the following protocol.

Transfected cells are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer [comprising 2 μCi of tracer $^{125}$I cAMP (100 μl) to 11 ml Detection Buffer] are prepared and maintained in accordance with the manufacturer's instructions. Assay Buffer is prepared fresh for screening and contained 20 mM HEPES, pH 7.4, 10 mM MgCl$_2$, 20 mM phospocreatine (Sigma), 0.1 units/ml creatine phosphokinase (Sigma), 50 μM GTP (Sigma), and 0.2 mM ATP (Sigma). Assay Buffer is then stored on ice until utilized.

Candidate compounds (if frozen, thaw at room temperature) are added, preferably, to 96-well plate wells (3 μl/well; 12 μM final assay concentration), together with 40 μl Membrane Protein (30 μg/well) and 50 μl of Assay Buffer. This admixture is then incubated for 30 minutes at room temperature, with gentle shaking.

Following the incubation, 100 μl of Detection Buffer is added to each well, followed by incubation for 2-24 hours. Plates are then counted in a Wallac MicroBeta™ plate reader using "Prot. #31" (as per manufacturer instructions).

By way of example and not limitation, a representative screening assay plate (96 well format) result is presented in FIG. 1. Bach bar represents the result for a compound that differs in each well, the "target receptor" being a Gsα Fusion Protein construct of an endogenous, constitutively active Gs-coupled GPCR The representative results presented in FIG. 1 also provide standard deviations based upon the mean results of each plate ("m") and the mean plus two arbitrary preference for selection of inverse agonists as "leads" from the primary screen involves selection of candidate compounds that that reduce the per cent response by at least the mean plate response, minus two standard deviations. Conversely, an arbitrary preference for selection of agonists as "leads" from the primary screen involves selection of candidate compounds that increase the per cent response by at least the mean plate response, plus the two standard deviations. Based upon these selection processes, the candidate compounds in the following wells were directly identified as putative inverse agonist (Compound A) and agonist (Compound B) to said endogenous GPCR in wells A2 and G9, respectively. See, FIG. 1. It is noted for clarity: these compounds have been directly identified without any knowledge of the endogenous ligand for this GPCR. By focusing on assay techniques that are based upon receptor function, and not compound binding affinity, we are able to ascertain compounds that are able to reduce the functional activity of this receptor (Compound A) as well as increase the functional activity of the receptor (Compound B).

Example 7

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at 5.5×10$^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 μl DMSO and 467 μl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 μl of 4 μM Fluo4-AM/ 2.5 mM Probenicid (Sigma, #P8761)/20 mM HEPES/complete medium at pH 7.4. Incubation at 37° C./5% CO$_2$ is allowed to proceed for 60 min.

After the 1 hr incubation, the Fluo4-AM incubation buffer is removed and the cells are washed 2× with 100 μl wash buffer. In each well is left 100 μl wash buffer. The plate is returned to the incubator at 37° C./5% CO$_2$ for 60 min.

FLIPR (Fluorometric Imaging Plate Reader; Molecular Device) is programmed to add 50 μl candidate compound on the 30$^{th}$ second and to record transient changes in intracellular calcium concentration ([Ca$^{2+}$]) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target Receptor further comprise promiscuous G alpha 15/16 or the chimeric Gq/Gi alpha unit.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example 8

Melanophore Technology

Melanophores are skin cells found in lower vertebrates. They contain pigmented organelles termed melanosomes.

Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this revispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods will be followed according to the disclosure of U.S. Pat. No. 5,462,856 and U.S. Pat. No. 6,051,386. These patent disclosures are hereby incorporated by reference in their entirety.

The cells are plated in 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7×L-15 (Gibco). After one hour, the cells in serum-free media remain in a pigment-dispersed state while the melatonin-treated cells are in a pigment-aggregated state. At this point, the cells are treated with a dose response of a candidate compound. If the plated GPCRs bind to the candidate compound, the melanophores would be expected to undergo a color change in response to the compound. If the receptor is either a Gs or Gq coupled receptor, and if the candidate compound is an agonist, then the melatonin-aggregated melanophores would undergo pigment dispersion. In contrast, if the receptor is a Gi-coupled receptor, and if the candidate compound is an agonist, then the pigment-dispersed cells would be expected to undergo a dose-dependent pigment aggregation.

Example 9

Tissue Distribution of Human RUP41

A. Affymetrix GeneChip® Technology

Amino acid sequences were submitted to Affymetrix for the designing and manufacturing of microarray containing oligonucleotides to monitor the expression levels of G protein-coupled receptors (GPCRs) using their GeneChip® Technology. Also present on the microarray were probes for characterized human brain tissues from Harvard Brain Band or obtained from commercially available sources. RNA samples were amplified, labeled, hybridized to the microarray, and data analyzed according to manufacturer's instructions.

Figure 2A:
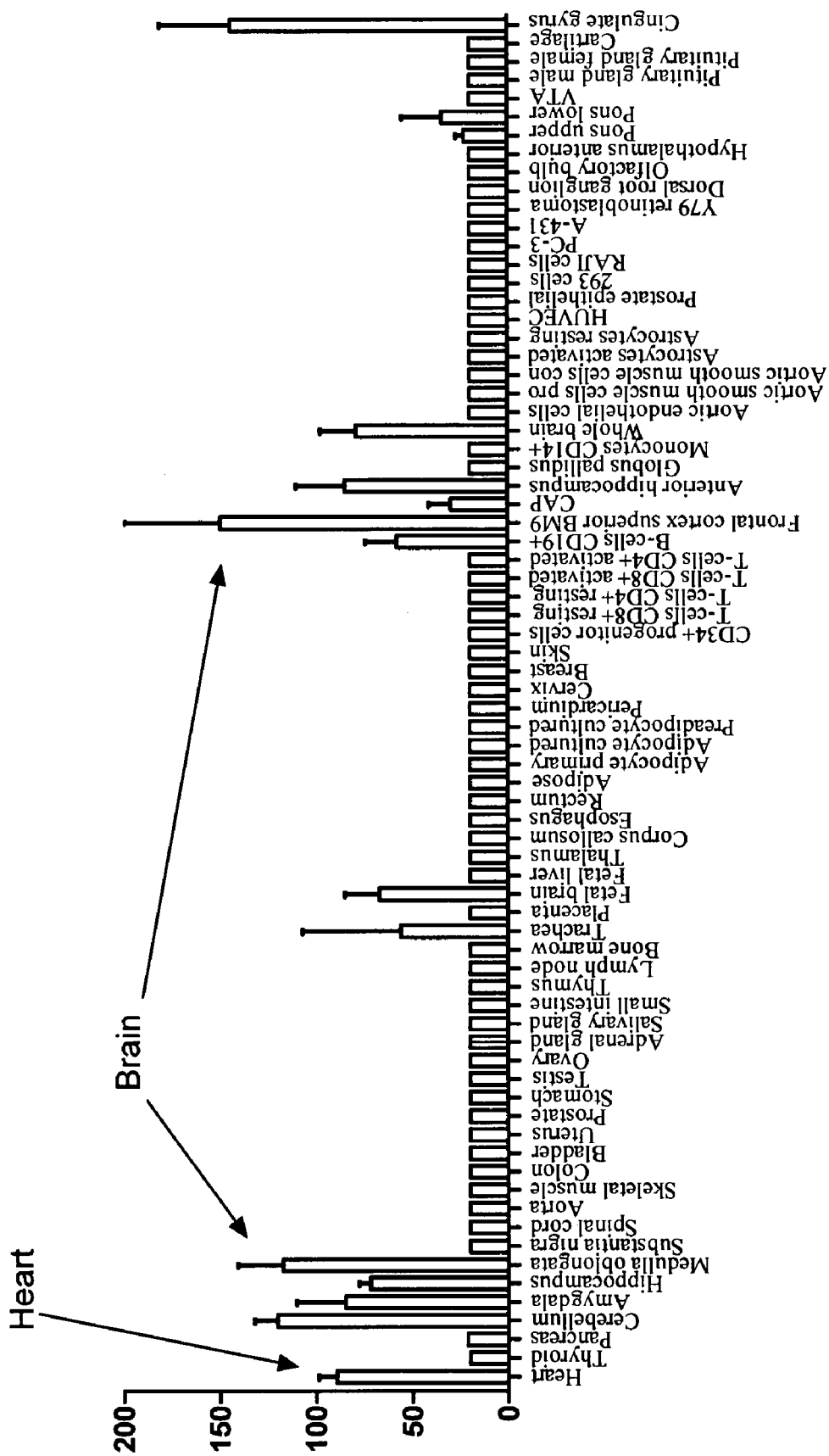
FIGS. 2A-C. A. Microarray analysis was performed on human tissue samples using a custom high-density oligonucleotide microarray, which contains probes that monitor the gene expression levels of RUP41. Histogram indicates the relative expression levels (Average Difference) and standard errors of duplicate measurements of RUP41 in each of the tissues profiled. Each tissue is identified in vertical text above its respective bar. Inspection of the histogram plot indicates expression of RUP41 in human brain and heart. B. Human multi-tissue dot blot demonstrates high-level expression of RUP41 mRNA in adult and fetal heart tissues. RUP41 mRNA expression is also detectable in a variety of regional brain tissues C. Human multi-tissue northern blot demonstrates high-level expression of RUP41 mRNA in heart and brain.

Using the GeneChip, the expression profile of human RUP41 was interrogated. See FIG. 2A. FIG. 2A is a plot representing the expression level of human RUP41 in various tissues. Inspection of the plot indicates expression of RUP41 in brain and heart. In tissues apart from brain, RUP41 is selectively expressed by heart. Selective expression of RUP41 affords diminished opportunity for potentially undesirable side effects by modulators of RUP41.

Figure 2C:
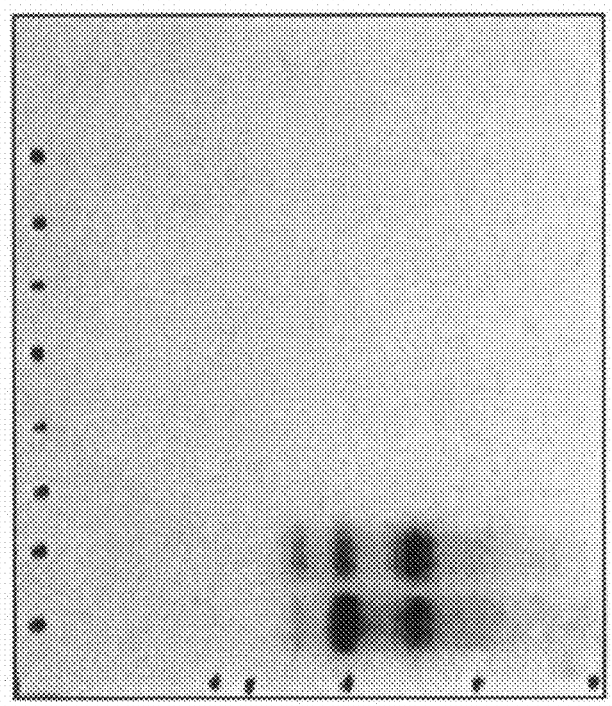
Figure 2B:
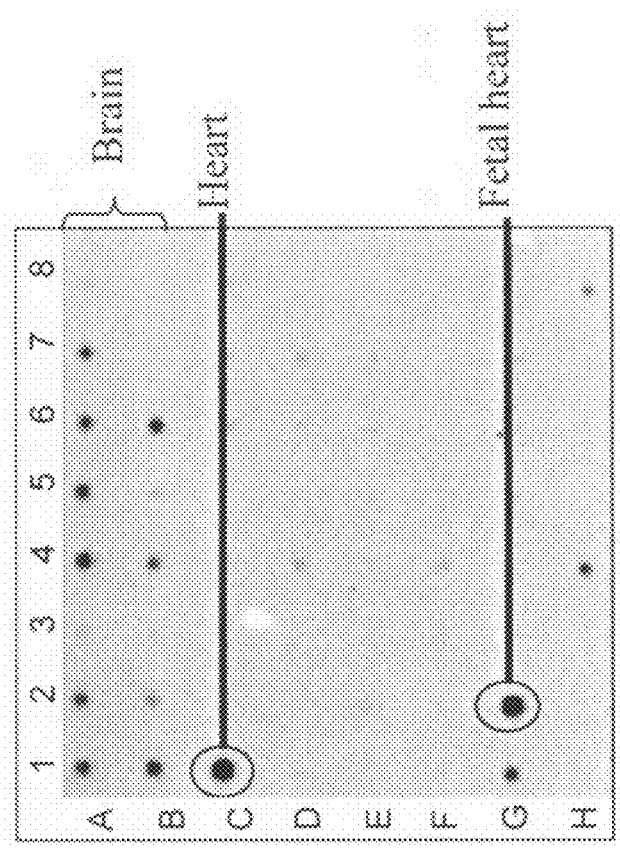

Results from dot blot (FIG. 2B) and Northern blot (FIG. 2C) are consistent with the results from GeneChip.

B. RT-PCR

RT-PCR was applied to interrogate the expression of human RUP41. Oligonucleotides used were RUP41-specific, and cDNA was used as template. Taq DNA polymerase (Stratagene) was utilized for the amplification in a 40 μl reaction according to the manufacturer's instructions. PCR conditions were 96° C. for 2 min, followed by 30 cycles of 96° C. for 30 sec, 55° C. for 30 sec, and 72° C. for 2 min, followed by 72° C. for 10 min. 20 μl of the reaction was loaded onto a 1.5% agarose gel to analyze the RT-PCR products.

The 5' PCR primer has the sequence:

```
5'-GTAATAATTGCCCTCCGGCGAGC-3'.        (SEQ ID NO:11)
```

The 3' PCR primer has the sequence:

```
5'-CTAGTCTGTGACAACCTGAGG-3'.          (SEQ ID NO:12)
```

The amplified DNA fragment is of size 390 base pairs.

Figure 7:
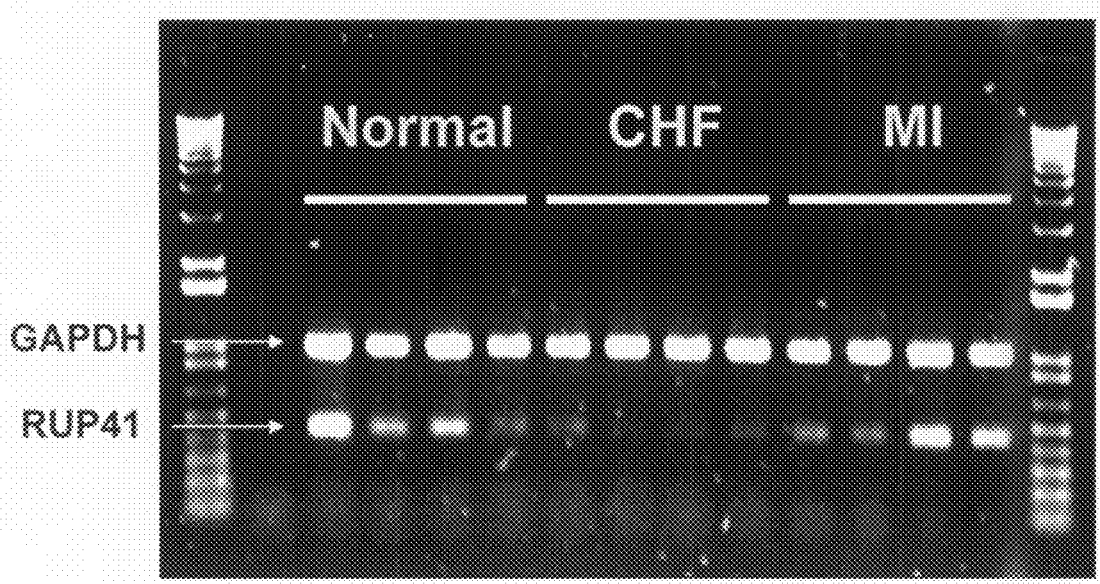
FIGS. 7A-B. A. RT-PCR was performed on total RNA isolated from human hearts. RUP41 transcript levels are decreased in RNA from patients with congestive heart failure (CHF) compared to patients with normal heart function (normal). Human GAPDH primers were added to each PCR reaction as internal controls for concentration of template and loading consistency. B. *Anova statistical analysis demonstrates a significant reduction of RUP41 transcript in CHF patients vs. normals at $p<0.05$. RUP41 transcript levels in patients with myocardial infarction (MI) are not different from normal hearts.
Figure 7:
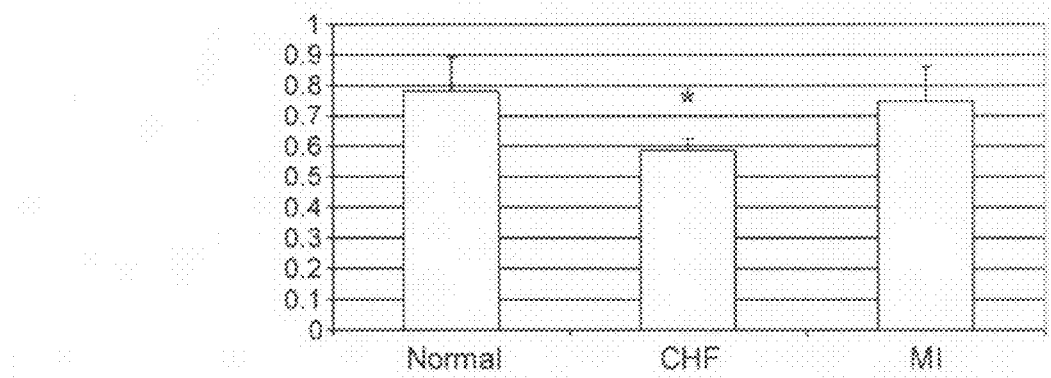

By way of illustration, RT-PCR for human RUP41 is shown in FIG. 7, infra, where expression of RUP41 in heart tissue from patients with congestive heart failure is compared with expression of RUP41 in heart tissue from patients with normal heart function.

Those skilled in the art are credited with the ability to analogously carry out RT-PCR for mouse RUP41 and rat RUP41.

C. Northern Blot

Northern blot analysis of human RUP41 expression was carried out by procedures well known to those skilled in the art. Human RUP41 coding region fragment corresponding to nucleotides 1,104-1,538 of SEQ ID NO:1 was used a probe.

Example 10

In Situ Hybridization: RUP41 Expression in Adult Rat Heart

Figure 3:
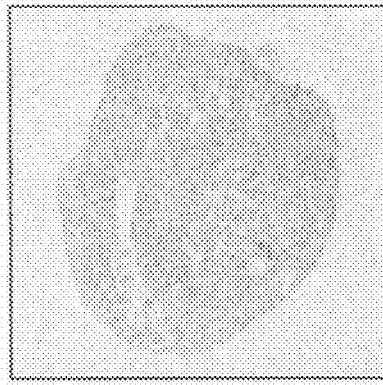
FIG. 3. In situ hybridization demonstrates broad myocardial expression of RUP41 in adult rat heart. Antisense RUP41 radiolabeled probes detect RUP41 expression in all chambers of the heart. Antisense control (GAPDH) and atrial specific (atrial natriuretic factor, ANF) probes were used on additional sections to demonstrate specificity of probe labeling of heart sections.
Figure 3:
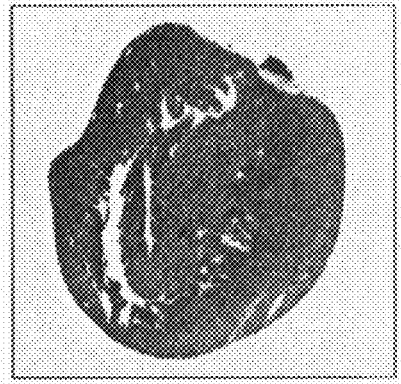
Figure 3:
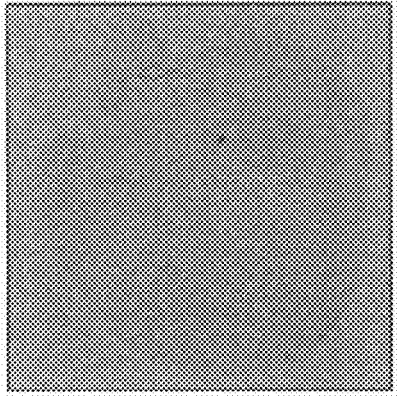
Figure 3:
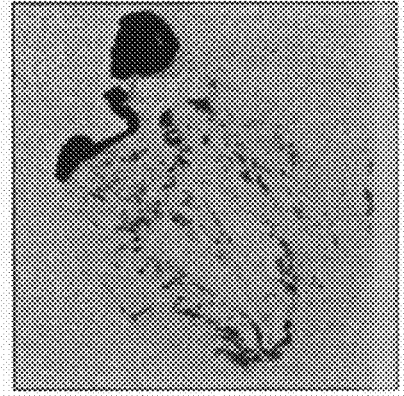
Figure 3:
Figure 3:

In situ hybridization demonstrated broad myocardial expression in adult rat heart (FIG. 3). Antisense RUP41 radiolabeled probes detect RUP41 expression in all chambers of the heart. Antisense control (GAPDH) and atrial specific (atrial natriuretic factor, ANF) probes were used on additional sections to demonstrate specificity of probe labeling of heart sections.

In Situ Hybridization

Fixed heart tissue was embedded in a 50:50 mixture of OCT:Aqua Mount (VWR, #41799-008, West Chester, Pa.) and frozen in dry ice/ethanol. The blocks were kept at −80° C. until cryosectioning, at which point 10 micron serial sections were prepared. After cryosectioning, the tissue sections were stored at −20° C. in sealed slide boxes.

Rat RUP41 polynucleotide of SEQ ID NO:6 was subcloned into PCRII-TOPO vector (Invitrogen, Carlsbad, Calif.) at a site flanked by SP6 and T7 promoters. [$^{35}$S]-radiolabeled antisense rat RUP41 mRNA probe complementary to the polynucleotide of SEQ ID NO:6 was prepared using SP6 RNA polymerase from Promega RiboProbe Transcription Kit (#P1460; Madison, Wis.), essentially as per the manufacturer's instructions. Control radiolabeled sense probe was prepared analogously using T7 RNA polymerase.

Fixed tissue sections were thawed and immediately subjected to a series of post-fix incubations at room temperature: PBS for 3 min; 10% formalin for 10 min; PBS for 10 min; and PBS for 10 min.

The tissue sections were then subjected to permeabilization and acetylation. To this end, the tissue sections were incubated with Proteinase K (0.001% Proteinase K in 0.5M Tris, 0.25M EDTA, pH 8.0) for 10 min at 37° C., followed by a wash with water for 5 min at room temperature. The tissue sections were then incubated for 5 min at room temperature with triethanolamine buffer (0.1M TEA, pH 8.0), followed by incubation for 5 min at room temperature with 2.5% acetic anhydride in 0.1M TEA pH 8.0. The tissue sections were then incubated at room temperature for 2 min each with: 2×SSC; 50% ethanol; 95% ethanol; and 100% ethanol. The tissue sections were then air dried and kept under desiccation until hybridization the following day.

Hybridization of the tissue sections was carried out for 20 hours at 60° C. in 0.47M NaCl, 54% formamide in a volume of 80-100 μl per section. Radiolabled probe was used at 1×10$^7$ cpm/ml. The tissue sections were then washed four times with 4×SSC at room temperature for 10 min each time. Unhybridized probe was digested on incubation with RNase A (20 μg/ml in 0.5M NaCl, 10 mM Tris, 1 mM EDTA, pH 8.0) for 30 min at 37° C. The tissue sections were then washed two times with 2×SSC at room temperature for 5 min each time, followed by a wash with 1×SSC at room temperature for 10 min, followed by a wash with 0.5×SSC at room temperature for 10 min. The tissue sections were then washed with 0.1× SSC at 65° C. for 30 min, followed by a wash with 0.1×SSC at room temperature for 5 min, followed by dehydration in alcohol.

Tissue sections which had undergone hybridization were then exposed to X-ray film and the RUP41 hybridization signal visualized by autoradiography. To this end, the tissue sections were exposed to Biomax MR film for 1 day, 4 days, and then 1 week. After autoradiography, the tissue sections were emulsion dipped using NTB-2 liquid emulsion (VWR, #IB1654433, West Chester, Pa.). The emulsion dipped tissue sections were exposed to the emulsion for 1 week and then developed. After development, the tissue sections were counterstained with bisbenzimide (0.001% in PBS) and coverslipped. The tissue sections were photographed using a darkfield condenser (silver grains appear white) and DAPI filter cube (to observe fluorescent bisbenzimide counterstain).

Identical methods were used radiolabel and hybridize probes generated from partial rat sequences for GAPDH and atrial natriuretic factor (ANF).

Example 11

Down-Regulation of RUP41 in Hypertrophied Neonatal Rat Ventricular Myocytes

Neonatal rat ventricular myocytes (NRVMs) were prepared as described previously [Adams, J W et al., J Biol Chem (1996) 271:1179-86; the disclosure of which is hereby incorporated by reference in its entirety]. Briefly, hearts were obtained from 1- to 2-day old Sprague-Dawley rat pups and digested with collagenase, and myocytes were purified by passage through a Percoll gradient. Cells were plated onto tissue culture dishes precoated with 1% gelatin and maintained overnight in 4:1 DMEM/medium-199 supplemented with 10% horse serum, 5% fetal calf serum, and antibiotics (100 units/ml penicillin and 100 μg/ml streptomycin. After 18 hours in plating medium, myocytes were washed with maintenance medium (DMEM/medium 199 plus antibiotics) to remove dead cells and debris and refreshed with maintenance medium for the duration of the experiment.

Figure 4:
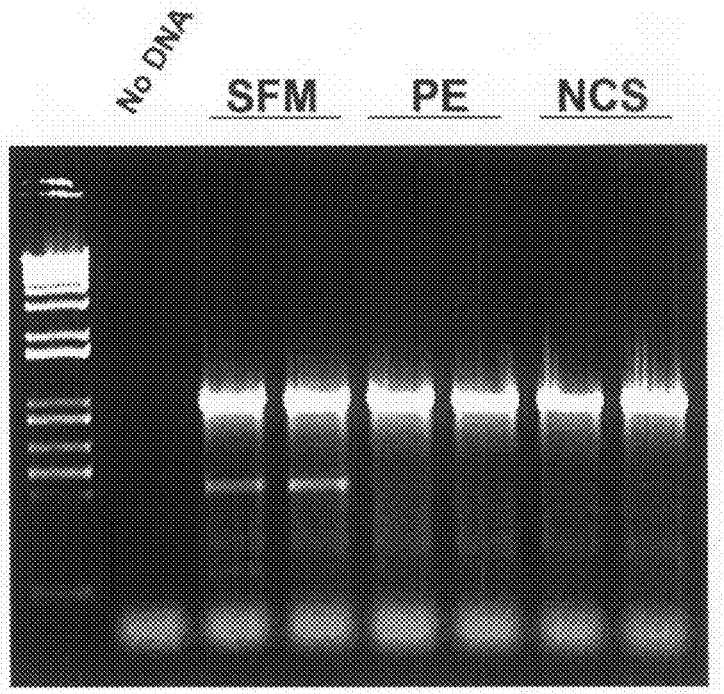
FIGS. 4A-B. A. RT-PCR demonstrates expression of RUP41 transcript in neonatal rat ventricular myocytes (NRVMs) maintained under serum free conditions for 24 hours. RUP41 transcript levels drop dramatically 24 hours following addition of phenylephrine (PE) or newborn calf serum (NCS) to media and correlates to the hypertrophic phenotype. G3PDH PCR product demonstrates equal levels of template used for the PCR reaction and consistency of gel loading. B. Northern blot demonstrates decreased level of RUP41 mRNA expression in NRVMs following 24 hour treatment with hypertrophic agents including, phenlyephrine (PE), phorbol 12-myristate 13-acetate (PMA), prostaglandin F2α (PGF2α), and newborn calf serum (NCS). Atrial natriuretic factor (ANF), a genetic marker of cardiomyocyte hypertrophy is upregulated in response to all hypertrophic stimuli. Methylene blue staining of 28S rRNA demonstrates integrity and equal loading of RNA.
Figure 4:
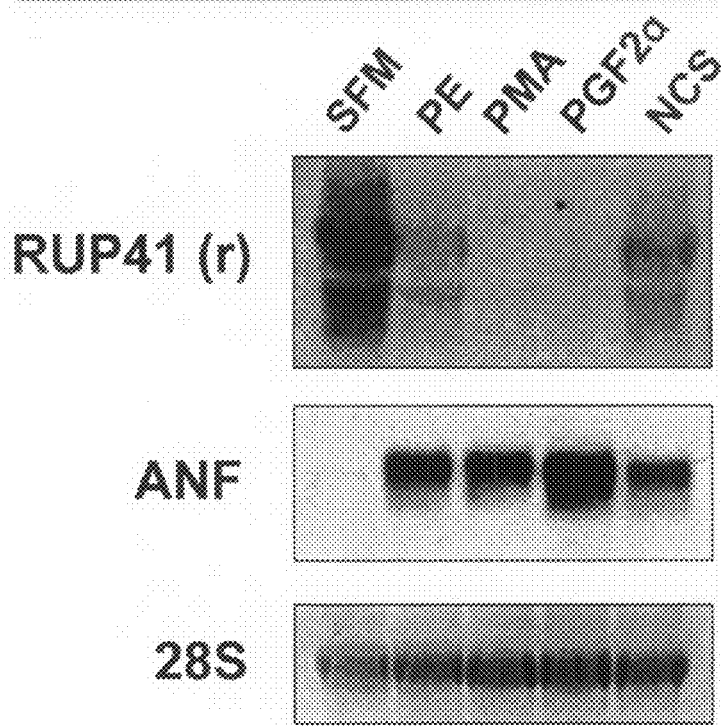

FIG. 4A. RT-PCR demonstrated expression of RUP41 transcript in neonatal rat ventricular myocytes (NRVMs) maintained under serum free conditions for 24 hours. RUP41 transcript levels drop dramatically 24 hours following addition of phenylephrine (PE) or newborn calf serum (NCS) to media and correlates to the hypertrophic phenotype. Phenylephrine was used at 100 μM (plus 2 μM to block beta-Adrenergic receptors and thereby allow selective activation of the alpha-Adrenergic receptor). Newborn calf serum was used at 10%. G3PDH PCR product demonstrates equal levels of template used for the PCR reaction and consistency of gel loading.

RT-PCR

Total RNA isolated from NRVMs as described above was used as a template for generation of reverse transcribed DNA (RT-DNA) using the RT for PCR kit (Becton Dickenson) according to manufacturers instructions. RUP41 expression was detected in RT-DNA samples by PCR. PCR conditions were 96° C. for 2 min, followed by 30 cycles of 96° C. for 30 sec, 55° C. for 30 sec, and 72° C. for 2 min, followed by 72° C. for 10 min. 20 μl of the reaction was loaded onto 1.5% agarose gel to analyze the RT-PCR products.

The 5' PCR primer has the sequence:

```
5'-GTAATAATTGCCCTCCGGCGAGC-3'.        (SEQ ID NO:11)
```

The 3' PCR primer has the sequence:

```
5'-CTAGTCTGTGACAACCTGAGG-3'.          (SEQ ID NO:12)
```

The amplified DNA fragment is of size 390 base pairs.

FIG. 4B. Northern blot demonstrated decreased level of RUP41 mRNA expression in NRVMs following 24 hour treatment with hypertrophic agents including, phenlyephrine (PE), phorbol 12-myristate 13-acetate (PMA), prostaglandin F2α (PGF2α), and newborn calf serum (NCS). Phenylephrine was used at 100 μM (plus 2 μM to block beta-Adrenergic receptors and thereby allow selective activation of the alpha-Adrenergic receptor). Phorbol 12-myristate 13-acetate was used at 100 nM. Prostaglandin F2α was used at 1 μM. Newborn calf serum was used at 10%. Atrial natriuretic factor (ANF), a genetic marker of cardiomyocyte hypertrophy is upregulated in response to all hypertrophic stimuli. Methylene blue staining of 28S rRNA demonstrates integrity and equal loading of RNA.

Northern Blot Analysis 1-2 day old rat (Sprague-Dawley) ventricular myocytes (NRVMs) were isolated and plated on culture dishes as previously described. Following various treatments, total RNA was isolated using Trizol reagent (Invitrogen) according to manufacturer's instructions. 15 micrograms of total RNA was separated electrophoretically on formaldehyde containing agarose gels and transferred to PVDF membranes (Amersham). Rat RUP41 coding region fragment corresponding to nucleotides 53-488 of SEQ ID NO:6 was used as probe for the Northern blot analysis. $^{32}$P-labeled probes were generated using standard methods and hybridized to membranes at 55° Celsius. Membranes were washed at high stringency and exposed to x-ray film for 2-4 days at −80° Celsius.

Example 12

Figure 5:
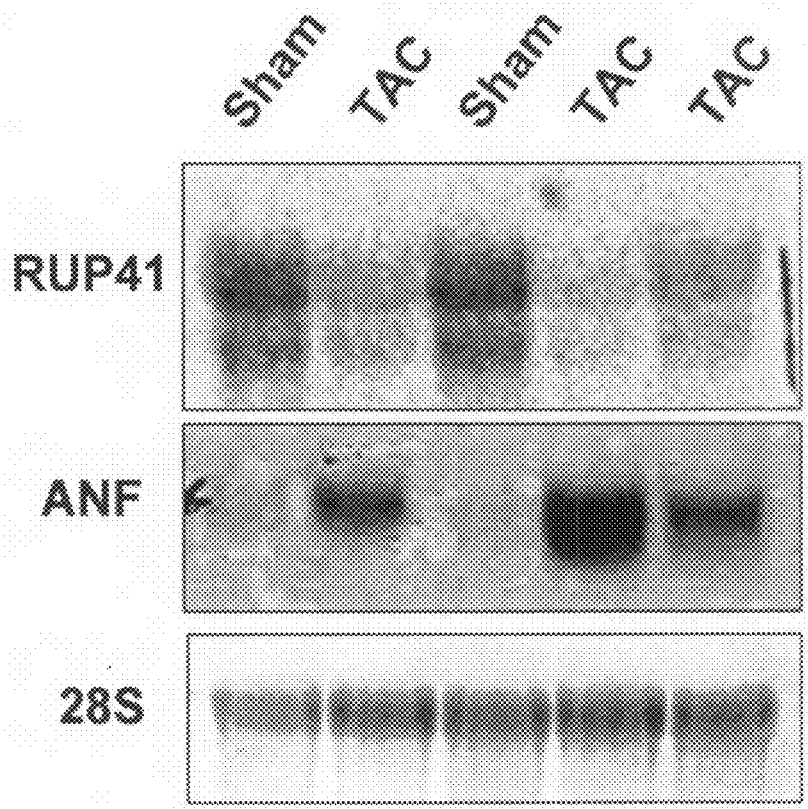
FIG. 5. Top. RUP41 mRNA is downregulated in an in vivo mouse model of pressure overload induced cardiac hypertrophy. Northern blot analysis was performed on total RNA isolated from left ventricles of mice subjected to transverse aortic constriction (TAC) or sham operated mice (SHAM) for 7 days. Increased ANF expression demonstrates formation of a genuine hypertrophic response in TAC hearts. Methylene blue staining of 28S rRNA demonstrates integrity and equal loading of RNA. Bottom. RUP41 signal was analyzed densitometrically and normalized to 28S rRNA signal. *Anova statistical analysis of 6 sham and 6 TAC samples demonstrated a significant reduction of RUP41 mRNA at $P<0.00005$.
Figure 5:
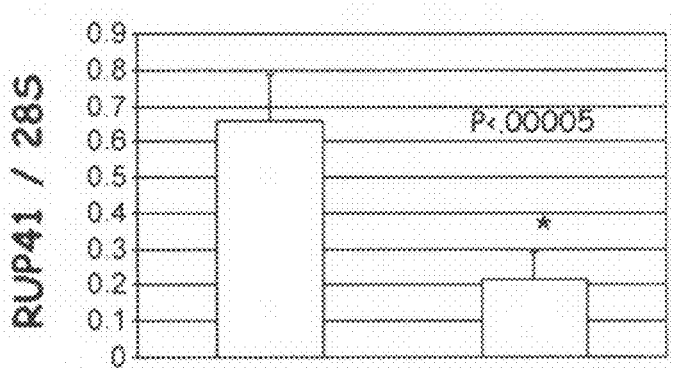

Down-Regulation of RUP41 in Mouse Hearts Subjected to Pressure Overload Hypertrophy FIG. 5 Top. RUP41 mRNA was downregulated in an in vivo mouse model of pressure overload induced cardiac hypertrophy. Northern blot analysis was performed on total RNA isolated from left ventricles of mice subjected to transverse aortic constriction (TAC) or sham operated mice (SHAM) for 7 days. Increased ANF expression demonstrates formation of a genuine hypertrophic response in TAC hearts. Methylene blue staining of 28S rRNA demonstrates integrity and equal loading of RNA. Mouse RUP41 coding region fragment corresponding to nucleotides 775-1,269 of SEQ ID NO:4 was used as probe for the Northern blot analysis. $^{32}$P-labeled probes were generated using standard methods and hybridized to membranes at 55° Celsius. Membranes were washed at high stringency and exposed to x-ray film for 2-4 days at −80° Celsius.

FIG. 5 Bottom. RUP41 signal was analyzed densitometrically and normalized to 28S rRNA signal. *Anova statistical analysis of 6 sham and 6 TAC samples demonstrated a significant reduction of RUP41 mRNA at $P<0.00005$.

Transverse Aortic Constriction (TAC)

Surgical constriction of the transverse aorta in mice was performed as previously described (Rockman et al, Proc Natl Acad Sci. 1991 Sep. 15; 88(18):8277-81). Briefly, 8 week old mice (C57/BL6) were anesthetized with a mixture of ketamine and xylazine. Under a dissecting microscope a midline cervical incision was made to expose the trachea and carotid arteries by microsurgical techniques. After successful endotracheal intubatin, the cannula was connected to a volume cuylced rodent ventilator (Harvard Apparatus) on supplemental oxygen with a tidal volume of 0.2 mL and respiratory rate of 110 per min. The chest cavity was entered in the second intercostal space at the left upper sternal border through a small incision, and aortic constriction was performed by tying a 7-0 nylon suture ligature against a 27-gauge needle to yield a narrowing 0.4 mm in diameter when the needle was removed and a reproducible transverse aortic constriction (TAC) of 65-70%. Following aortic banding the pneumothorax was evacuated and the animals were extubated and allowed to recover.

Example 13

Down-Regulation of RUP41 in NRVMs Subjected to Hypoxia

Figure 6:
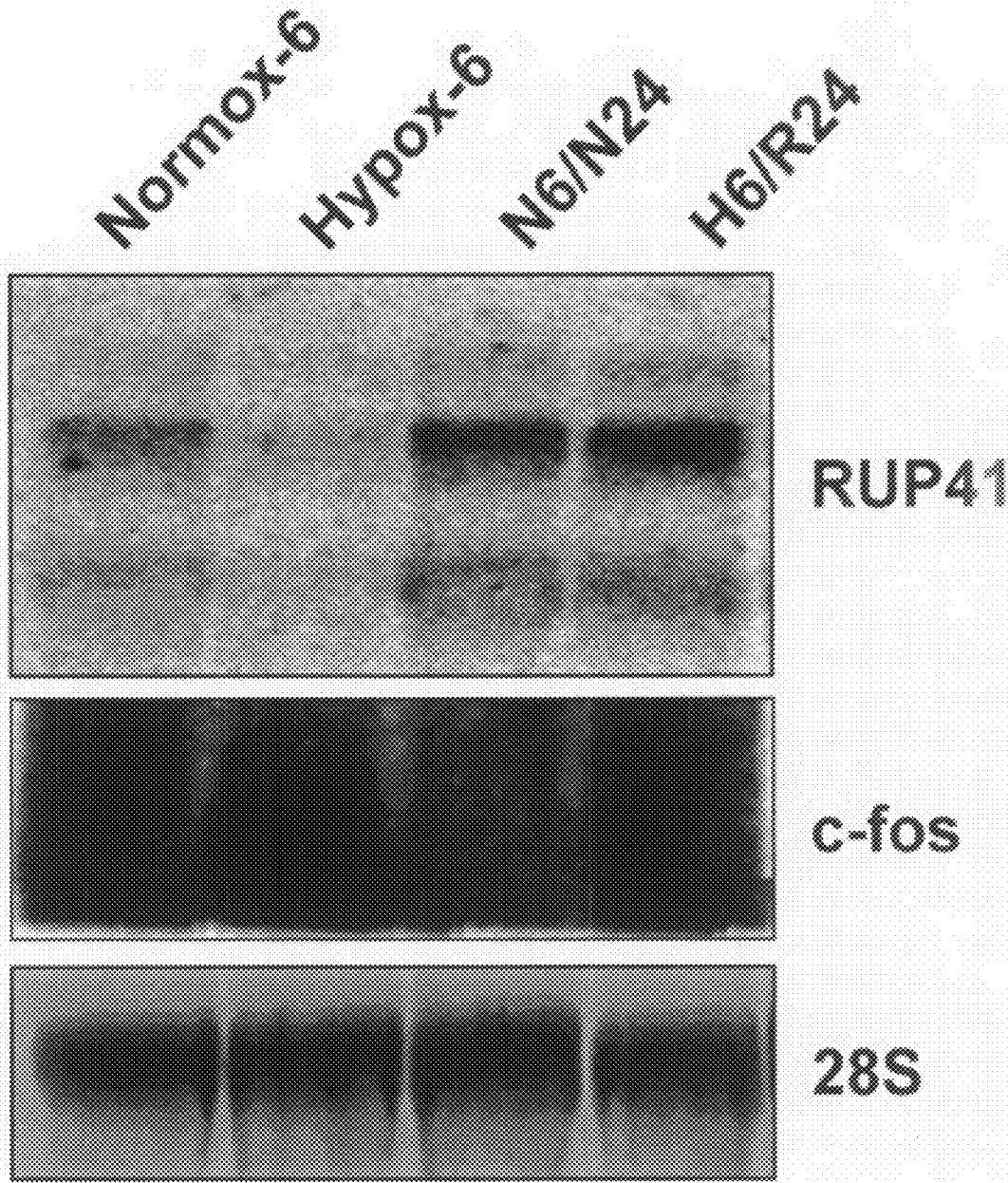
FIG. 6. Northern blot demonstrates that RUP41 mRNA levels are decreased in total RNA isolated from NRVMs subjected to hypoxia for 6 hours. RUP41 mRNA levels return to control (normoxia) levels after 24 hours of reoxygenation following hypoxia (H6/R24). Increased c-fos expression (Hypoxia-6) demonstrates myocyte stress response to hypoxic conditions. Methylene blue staining of 28S rRNA demonstrates integrity and equal loading of RNA.

Northern blot demonstrated that RUP41 mRNA levels are decreased in total RNA isolated from NRVMs subjected to hypoxia for 6 hours (FIG. 6). RUP41 mRNA levels return to control (normoxia) levels after 24 hours of reoxygenation following hypoxia (H6/R24). Increased c-fos expression (Hypoxia-6) demonstrates myocyte stress response to hypoxic conditions. Methylene blue staining of 28S rRNA demonstrates integrity and equal loading of RNA. Rat RUP41 coding region fragment corresponding to nucleotides 53-488 of SEQ ID NO:6 was used as probe for the Northern blot analysis. $^{32}$P-labeled probes were generated using standard methods and hybridized to membranes at 55° Celsius. Membranes were washed at high stringency and exposed to x-ray film for 2-4 days at −80° Celsius.

Hypoxia treatment of NRVMs is described in Van Heugten et al., J Mol Cell Cardiol (1994) 26:1513-24, the disclosure of which is hereby incorporated by reference in its entirety. Briefly, hypoxia was achieved using an airtight incubator infused with 95% N2 and 5% CO2. After hypoxia treatment for indicated times, cells were removed from chamber to ambient air and serum-free DMEM/F12 media was refreshed. Also see Example 17, infra.

Example 14

Down-Regulation of RUP41 in Humans with Congestive Heart Failure

FIG. 7A. RT-PCR was performed on total RNA isolated from human hearts. RUP41 transcript levels are decreased in RNA from patients with congestive heart failure (CHF) compared to patients with normal heart function (normal). Human GAPDH primers were added to each PCR reaction as internal controls for concentration of template and loading consistency.

FIG. 7B. *Anova statistical analysis demonstrates a significant reduction of RUP41 transcript in CHF patients vs. normals at $p<0.05$. RUP41 transcript levels in patients with myocardial infarction (MI) are not different from normal hearts.

Human Heart Disease Samples

RT-PCR (see above) was performed from total RNA from hearts taken at autopsy of human patients diagnosed with normal heart function, congestive heart failure (CHF), and myocardial infarction (MI) obtained commercially (Clinomics). Relative levels of RUP41 expression were determined in each group after normalizing to GAPDH internal controls.

Example 15

RUP41 Couples to Gi in COS-7 Cells

Figure 8:
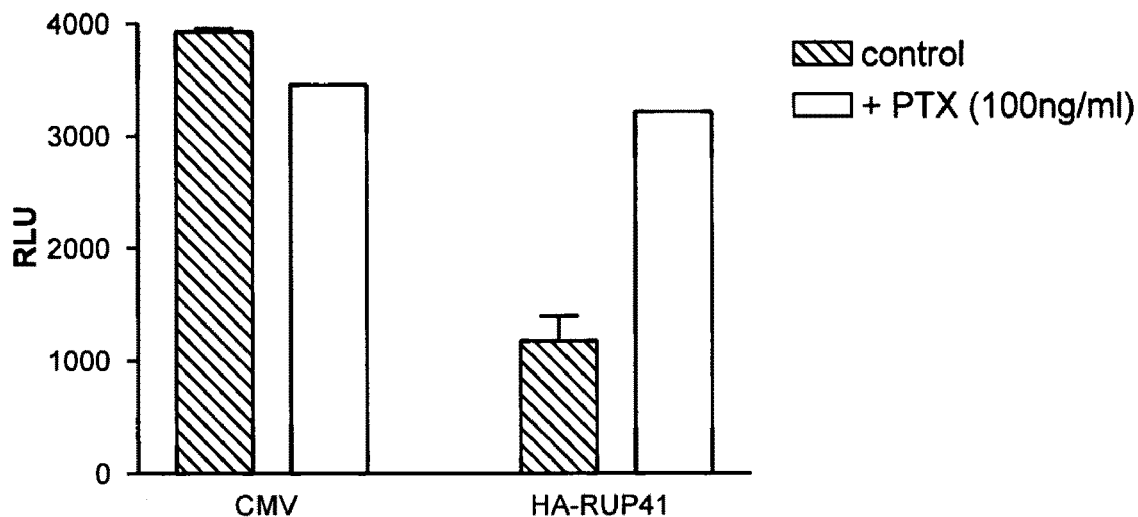
FIG. 8. Top. COS-7 cells were co-transfected with pCMV-HARUP41 (HA-RUP41) or pCMV-HA backbone (CMV) and a constitutively active Gs-coupled Thyroid Stimulating Hormone Receptor (pCMV-CART-TSHR). [HARUP41 corresponds to hemagglutinin (HA)-tagged RUP41.] In addition, a CRE-Luciferase reporter construct was co-transfected to determine activity of cAMP activated pathways in the presence or absence of pertussis toxin (PIN. Luciferase reporter activity in cells co-expressing CART-TSHR and HARUP41 was lower than that in cells co-expressing CART-TSHR and pCMV-HA control, suggesting that RUP41 couples to Gi. The inhibition of cAMP reduction by RUP41 with PTX treatment verifies Gi coupling of this receptor. Bottom. COS-7 cells were transfected with pCMV-HA (CMV) or pCMV-HARUP41 (RUP41) constructs in the presence or absence of pertussis toxin (PTX). Forskolin (1 uM) stimulated increase in cAMP levels was inhibited by expression of RUP41. The inhibition of cAMP reduction by RUP41 with PTX treatment verifies Gi coupling of this receptor.
Figure 8:
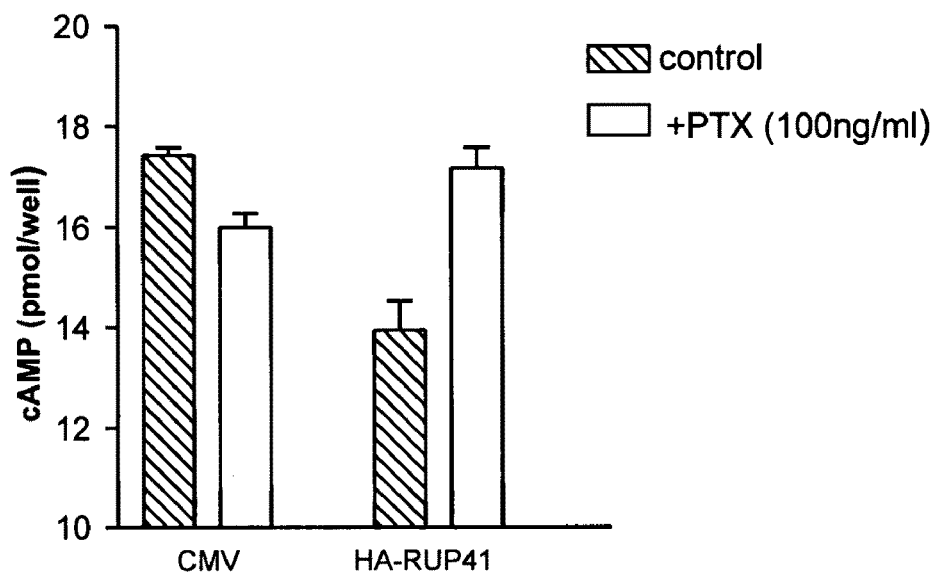

FIG. 8 Top. COS-7 cells were co-transfected with pCMV-HARUP41 (HA-RUP41) or pCMV-HA backbone (CMV) and a constitutively active Gs-coupled thyroid stimulating hormones receptor (pCMV-TSHR-A6231). [HARUP41 corresponds to hemagglutinin (HA)-tagged RUP41.] In addition, a CRE-Luciferase reporter construct was co-transfected to determine activity of cAMP activated pathways in the presence or absence of pertussis toxin (PTX). Luciferase reporter activity in cells co-expressing CART-TSHR and HARUP41 was lower than that in cells co-expressing CART-TSHR and pCMV-HA control, suggesting that RUP41 couples to Gi. The inhibition of cAMP reduction by RUP41 with PTX treatment verifies Gi coupling of this receptor.

FIG. 8 Bottom. COS-7 cells were transfected with pCMV-HA (CMV) or pCMV-HARUP41 (RUP41) constructs in the presence or absence of pertussis toxin (PTX). Forskolin (1 μM) stimulated increase in cAMP levels was inhibited by expression of RUP41. The inhibition of cAMP reduction by RUP41 with PTX treatment verifies Gi coupling of this receptor.

RUP41 Vector Contruction—

Polynucleotide encoding amino acids 2-433 of human RUP41 polypeptide of SEQ ID NO:3 was ligated into pCMV-HA for transient transfection expression studies.

Transient Transfections

Transfection of DNA was performed using a 5'-HA tagged RUP41 expression construct (HA-pCMVRUP41). Briefly, HA-pCMVRUP41 was transfected into COS-7 or HEK cells plated on chamber slides using Fugene-6 transfection reagent according to manufacturer's instructions (Roche). 5'-HA tagged GPR (orphan GPCR; GenBank® Accession No. NM_007223) and HA-pCMV vector were transfected into COS-7 and HEK cells as controls.

cAMP Measurement 24 h following transfection of COS-7 cells with RUP41 expression plasmids cells were washed with PBS and incubated with serum-free medium with or without 100 ng/ml PTX at 37° C. for 18 h prior to harvesting cells for FlashPlate assay (PerkinElmer). cAMP levels were detected following manufacturers instructions.

CRE-Luciferase Reporter Assay 24 h following co-transfection of COS-7 cells with pCMVRUP41 and the TSHR-A623I expression plasmid (DNA ratio for TSHR-A623I: RUP41 (or CMV)=1:7(w/w). cells were washed with PBS and incubated with serum-free medium with or without 100 ng/ml PTX at 37° C. for 18 h prior to CRE reporter assay detection using LucLite Luciferase Reporter Assay kit (Packard) according to manufacturers instructions.

Example 16

Adenovirus-Mediated Over-Expression of RUP41 Promotes Survival of NRVMs

Figure 9:
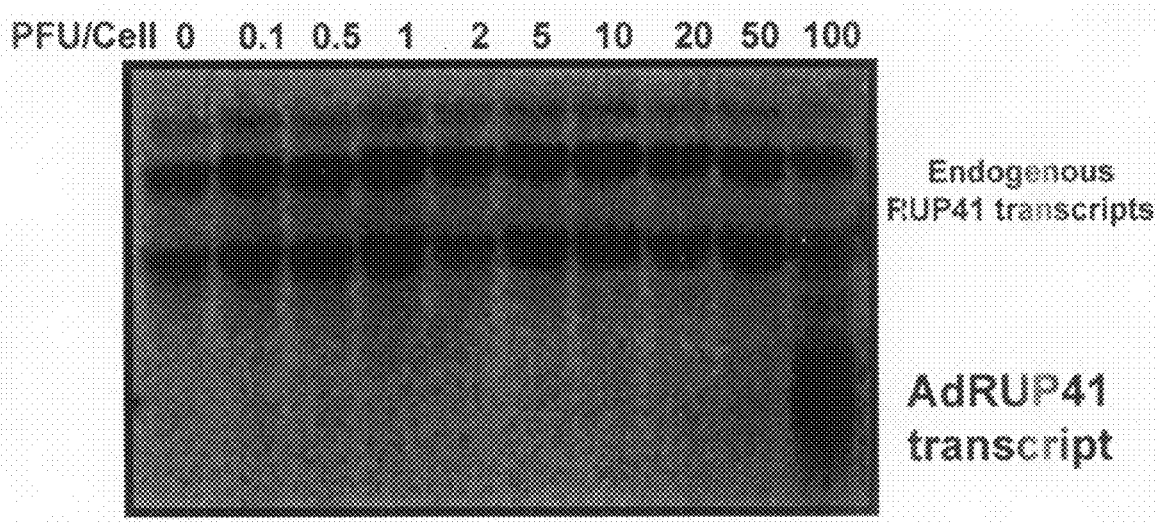
FIG. 9A-B. A. NRVMs were treated with recombinant adenovirus encoding RUP41 (AdRUP41) at various multiplicities of infection defined by the viral titer in plaque forming units (PFU) per cell. Twenty-four hours following adenovirus infection, total RNA was isolated and Northern blot analysis was used to determine levels of virally expressed RUP41. At 50 PFU/cell RUP41 expression was detectable, but high level expression was demonstrated at 100 PFU/cell. B. NRVMs infected with AdRUP41 at 100 PFU/cell for 48 hours demonstrated increased cell survival in serum free media. NRVMs were co-stained with Texas Red conjugated phalloidin and Hoechst 33342.
Figure 9:
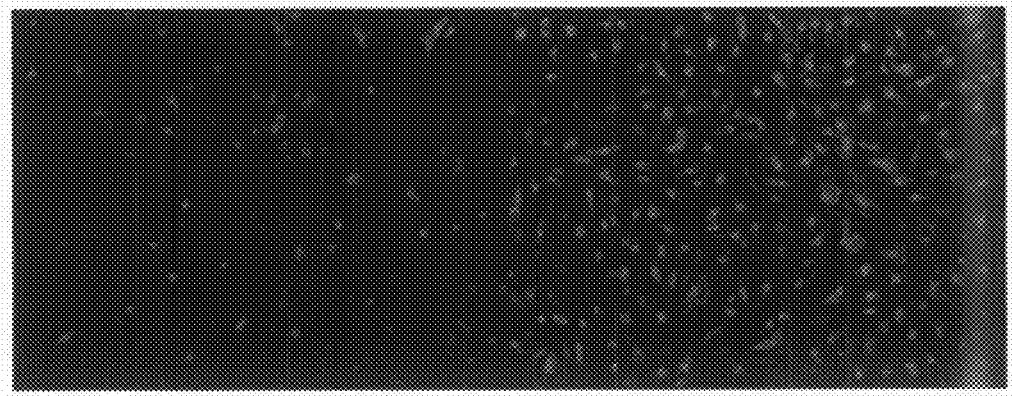

FIG. 9A. NRVMs were treated with recombinant adenovirus encoding RUP41 (AdRUP41) at various multiplicities of infection defined by the viral titer in plaque forming units (PFU) per cell. Twenty-four hours following adenovirus infection, total RNA was isolated and northern blot analysis was used to determine levels of virally expressed RUP41. At 50 PFU/cell RUP41 expression was detectable, but high level expression was demonstrated at 100 PFU/cell.

FIG. 9B. NRVMs infected with AdRUP41 at 100 PFU/cell for 48 hours demonstrated increased cell survival in serum free media. NRVMs were co-stained with Texas Red conjugated phalloidin and Hoechst 33342.

RUP41 Vector Construction

For adenovirus experiments, polynucleotide encoding human RUP41 polypeptide of SEQ ID NO:3 was subcloned into pShuttleCMV (Qbiogene) prior to generation of recombinant adenoviral RUP41 (AdRUP41).

Adenovirus Infections

Infection of NRVMs with adenovirus vectors was carried out as previously described [Adams J W et al., Circ Res (2000) 87:1180-7; the disclosure of which is hereby incorporated by reference in its entirety]. Briefly, NRVMs were cultured on laminin-coated (3.5 mg/cm$^2$) chamber slides (Nunc) overnight in the presence of serum, washed and incubated for a further 8 hours in serum-free media before adenovirus infection. Optimal multiplicity of infection (MOI) was determined to be 50-100 plaque forming units (PFU) per cell over a dose range of 0.1-500 PFU/cell. A MOI of 50 PFU/cell resulted in greater than 95% infection efficiency (as determined by GFP expression in NRVMs infected with this control virus) without any cytotoxic during the first 48 h following infection with either AdRUP41 or the control adenovirus encoding GFP (AdGFP).

Example 17

Over-Expression of RUP41 Rescues NRVMs from Hypoxia/Reoxygenation Induced Apoptosis Analysis of oligonucleosomal DNA fragmentation (aka laddering) demonstrated that reoxygenation (24 hours) following hypoxia (8 hours) stimulates increased apoptosis in NRVMs (H8/N24) infected with a control (AdGFP) adenovirus at 100 PFU/cell. However, adenovirus mediated overexpression of human RUP41 polypeptide of SEQ ID NO:3 (100 PFU/cell) reduces the level of DNA fragmentation induced by serum deprivation (normox) and reoxygenation following hypoxia (H8/N24) (FIG. 10).

Hypoxia/Reoxygenation

Isolated NRVMs were cultured in the presence of serum (10% FBS, 5% HS) overnight then media was replaced with serum-free media DMEM/F12 (Sigma) for 24 hours before hypoxia treatment. Hypoxia was achieved using an airtight incubator infused with 95% N2 and 5% CO2 [Van Heugten et al., J Mol Cell Cardiol (1994) 26:1513-24, the disclosure of which is hereby incorporated by reference in its entirety]. After hypoxia treatment for indicated times, cells were removed from chamber to ambient air and serum-free DMEM/F12 media was refreshed.

DNA Fragmentation

DNA was isolated from NRVMs using the PUREGENE DNA isolation kit according to manufacturer's instructions (Gentra). Equal amounts of DNA were separated on a 2% agarose and fragmentation was detected by staining with ethidium bromide under ultraviolet light.

Example 18

Cardioprotection

A modulator of the invention can be shown to be cardioprotective using the in vivo rat model of Fryer et al. [Circ Res (1999) 84:846-51; the disclosure of which is hereby incorporated by reference in its entirety]. Said modulator is administered by intraperitoneal injection. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. The placebo group is administered vehicle alone. In some embodiments, said modulator is agonist.

Male Wistar rats, 350 to 450 g, are used for all phases of this study. Rats are administered said modulator or saline 1, 12, 24, 48, or 72 hours before the surgical protocol through intraperitoneal injection. Subsequently, rats are anesthetized via intraperitoneal administration of thiobutabarbital sodium (Inactin, Research Biochemical International; 100 mg/kg). A tracheotomy is performed, and the trachea is intubated with a cannula connected to a rodent ventilator (model CIV-101, Columbus Instruments, or model 683, Harvard Apparatus). Rats are ventilated with room air supplemented with $O_2$ at 60-65 breaths per minute. Atelectasis is prevented by maintaining a positive end-expiratory pressure of 5 to 10 mm H2O. Arterial pH, $P_{CO2}$, and $P_{O2}$ are monitored at control, 15 minutes of occlusion, and 60 and 120 minutes of reperfusion by a blood gas system (AVL 995 pH/blood gas analyzer, AVL Medical Instruments) and maintained within a normal physiological range (pH 7.35 to 7.45; $P_{CO2}$ 25 to 40 mm Hg; and $P_{O2}$ 80 to 110 mm Hg) by adjusting the respiratory rate and/or tidal volume. Body temperature is maintained at 38° C. by the use of a heating pad, and bicarbonate is administered intravenously as needed to maintain arterial blood pH within normal physiological levels.

The right carotid artery is cannulated to measure blood pressure and heart rate via a Gould PE50 or Gould PE23 pressure transducer connected to a Grass (model 7) polygraph. The right jugular vein is cannulated for saline, bicarbonate, and drug infusion. A left thoracotomy is performed at the fifth intercostals space followed by a pericardiotomy and adjustment of the left atrial appendage to reveal the location of the left coronary artery. A ligature (6-0 prolene) is passed below the coronary artery from the area immediately below the left atrial appendage to the right portion of the left ventricle. The ends of the suture are threaded through a propylene tube to forma a snare. The coronary artery is occluded by pulling the ends of the suture taut and clamping the dnare onto the epicaridal surface with a hemostat. Coronary artery occlusion is verified by epicardial cyanosis and a subsequent decrease in blood pressure. Reperfusion of the heart is initiated via unclamping the hemostat and loosening the snare and is confirmed by visualizing an epicardial hyperemic response. Heart rate and blood pressure are allowed to stabilize before the experimental protocols are initiated.

Rats are randomly divided into the designated experimental groups. Control rats are administered saline 24 hours before 30 minutes of regional ischemia and 2 hours of reperfusion (I/R). To show acute cardioprotection induced by said modulator, said modulator is administered 1 hour before a prolonged ischemic insult. To show the delayed cardioprotection against an acute ischemic insult, said modulator is administered at the designated doses either 12 or 24 hours before I/R Said modulator is also administered at the designated doses either 48 or 72 hours before I/R.

On completion of the above protocols, the coronary artery is occluded, and the area at risk (AAR) is determined by negative staining with patent blue dye administered via the jugular vein. The rat is euthanized with a 15% KCl solution. The heart is excised and the left ventricle is dissected from the remaining tissue and subsequently cut into 6 thin, cross-sectional pieces. This allows for the delineation of the normal area, stained blue, versus the AAR, which subsequently remained pink. The AAR is excised from the nonischemic area, and the tissues are placed in separate vials and incubated for 15 minutes with 1.0% 2,3,5-triphenyltetrazolium chloride (TTC) stain in 100 mmol/L phosphate buffer (pH 7.4) at 37° C. TTC is an indicator of viable and nonviable tissue. TTC is reduced by dehydrogenase enzymes present in viable myocardium and results in a formazan precipitate, which induces a deep red color, whereas the infarcted area remains gray {Klein et al., Virchows Arch [Pathol Anat] (1981) 393:287-97}. Tissues are stored in vials of 10% formaldehyde overnight, and the infracted myocardium is dissected from the AAR under the illumination of a dissecting microscope (Cambridge Instruments). Infarct size (IS), AAR, and left ventricular weight (LV) are determined by gravimetric analysis. AAR is expressed as a percentage of the LV (AAR/LV), and IS is expressed as a percentage of the AAR (IS/AAR).

Rats are excluded from data analysis if they exhibit severe hypotension (<30 mm Hg systolic blood pressure) or if adequate blood gas values within a normal physiological range are unable to be maintained because of metabolic acidosis or alkalosis.

All values are expressed as mean±SEM. One-way ANOVA with Bonferroni's test is used to determine whether any significant differences exist among groups for hemodynamics, IS, and AAR. Significant differences are determined at $P<0.05$. A reduction of IS/AAR is indicative of cardioprotection.

Example 19

Oral Bioavailability

Physicochemico analytical approaches for directly assessing oral bioavailability are well known to those of ordinary skill in the art and may be used [see, e.g., without limitation: Wong P C et al., Cardiovasc Drug Rev (2002) 20:137-52; and Buchan P et al., Headache (2002) Suppl 2:S54-62; the disclosure of each of which is hereby incorporated by reference in its entirety]. By way of further illustration and not limitation, said alternative analytical approaches may comprise liquid chromatography-tandem mass spectrometry [Chavez-Eng C M et al., J ChromatogrB Analyt Technol Biomed Life Sci (2002) 767:117-29; Jetter A et al., Clin Pharmacol Ther (2002) 71:21-9; Zimmerman J J et al., J Clin Pharmacol (1999) 39:1155-61; and Barrish A et al., Rapid Commun Mass Spectrum (1996) 10:1033-7; the disclosure of each of which is hereby incorporated by reference in its entirety].

Positron emission tomography (PET) has been successfully used to obtain direct measurements of drug distribution, including oral bioavailability, in the mammalian body following oral administration of the drug [Gulyas et al., Eur J Nucl Med Mol Imaging (2002) 29:1031-8; the disclosure of which is hereby incorporated by reference in its entirety].

Alternatively, oral bioavailability of a modulator of the invention may be determined on the basis of in vivo data developed, as for example by way of illustration and not limitation through the rat model of Example 18. The modulator is administered by oral gavage at doses ranging from 0.1 mg kg$^{-1}$ to 100 mg kg$^{-1}$. Oral administration of the modulator is shown to confer cardioprotection. The effect of the modulator is shown to be dose-dependent and comparable to the effect after intraperitoneal administration. The dose of modulator required to achieve half-maximal reduction of IS/AAR through oral administration is compared to the dose of modulator required to achieve half-maximal reduction of IS/AAR through intraperitoneal administration. By way of illustration, if said oral dose is twice said intraperitoneal dose, then the oral bioavailability of the modulator is taken to be 50%. More generally, if said oral dose is $\theta$ mg kg$^{-1}$ and said intraperitoneal dose is $\rho$ mg kg$^{-1}$, then the oral bioavailability of the modulator as a percentage is taken to be $[(\rho/\theta)\times100]$.

It would be readily apparent to anyone of ordinary skill in the art that a determination of oral bioavailability of a modulator of the invention can be carried out using an in vivo animal model other than the one presented here for purposes of illustration and not limitation. It would also be readily apparent to anyone of ordinary skill in the art that the bioactivity readout for said oral bioavailability could be a parameter other than IS/AAR. It is readily envisioned that the reference route of administration may be other than intraperitoneal. In some embodiments, said reference route of administration may be intravenous.

In some embodiments, oral bioavailability of a modulator of the invention is at least 1%, at least 5%, at least 10%, at least 15%, at least 20%, at least 25%, at least 30%, at least 35%, at least 40%, or at least 45% relative to intraperitoneal injection.

Example 20

Transgenic Mouse/Rat/Pig Comprising Expression of a Human RUP41 GPCR

The present invention also provides methods and compositions relating to a transgenic non-human mammal comprising expression of a human RUP41 GPCR, said receptor comprising a polypeptide selected from the group consisting of:

(a) the polypeptide of SEQ ID NO:2;

(b) the polypeptide of SEQ ID NO:2 wherein the phenylalanine at amino acid position 312 of SEQ ID NO:2 is substituted with lysine;

(c) the polypeptide of SEQ ID NO:3; and (d) the polypeptide of SEQ ID NO:3 wherein the phenylalanine at amino acid position 312 of SEQ ID NO:3 is substituted with lysine.

In some embodiments, said non-human mammal is a mouse, rat, or pig.

Methods of making transgenic animals such as mice, rats, and pigs are well known to those of ordinary skill in the art, and any such method can be used in the present invention. Briefly, transgenic mammals can be produced, e.g., by transfecting a pluripotential stem cell such as an ES cell with a polynucleotide ("transgene") encoding a human RUP41 GPCR. Successfully transformed ES cells can then be introduced into an early stage embryo that is then implanted into the uterus of a mammal of the same species. In certain cases, the transformed ("transgenic") cells will comprise part of the germ line of the resulting animal and adult animals comprising the transgenic cells in the germ line can then be mated to other animals, thereby eventually producing a population of transgenic animals that have the transgene in each of their cells and that can stably transmit the transgene to each of their offspring. Other methods of introducing the polynucleotide can be used, for example introducing the polynucleotide encoding a human RUP41 GPCR into a fertilized egg or early stage embryo via microinjection. Alternatively, the transgene may be introduced into an animal by infection of zygotes with a retrovirus containing the transgene [Jaenisch, R, Proc Natl Acad Sci USA (1976) 73:1260-4]. Methods of making transgenic mammals are described, e.g., in Wall et al., J Cell Biochem (1992) 49:113-20; Hogan et al., in Manipulating the Mouse Embryo. A Laboratory Manual. (1986) Cold Spring Harbor Laboratory Press, Cold Spring Harbor, N.Y.; in Costa et al., FASEB J (1999) 13:1762-73; in WO 91/08216; in U.S. Pat. No. 4,736,866; and in U.S. Pat. No. 6,504,080; the disclosure of each of which is hereby incorporated by reference in its entirety.

In some embodiments, said expression of a human RUP41 GPCR is cardiomyocyte-selective. In some embodiments, said cardiomyocyte-selective expression of said human RUP41 GPCR is conferred by alpha myosin heavy chain promoter [Subramaniam A et al., J Biol Chem (1991) 266: 24613-20; the disclosure of which is hereby incorporated by reference in its entirety].

Example 21

Transgenic In Vivo Animal Model of Cardioprotection

A compound of the present invention can be shown to have efficacy for cardioprotection using a transgenic in vivo animal model described in Example 20. In some embodiments, said animal is mouse, rat or pig.

Said compound can be assessed for efficacy for cardioprotection by administering said compound to said transgenic animal and determining if said administration leads to a reduction in IS/AAR in the in vivo rat model of Example 18 or an in vivo model in mouse or pig analogous thereto relative to said transgenic animal administered vehicle alone.

In preferred embodiments, said compound is modulator of the invention. In some embodiments, said modulator lowers the intracellular level of cAMP. In some embodiments, said modulator is an agonist. In some embodiments, said compound is administered by intraperitoneal injection. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. The placebo group is administered vehicle alone. In some embodiments, said dose is administered daily. In some embodiments, said dose is administered for a period selected from the group of one week, two weeks, three weeks, and four weeks. It is noted that this route of administration, these dosage ranges, this frequence of dose administration, and this duration of dose administration are intended to be illustrative and not limiting to the invention.

Example 22

Mouse/Rat/Pig Comprising Knockout of RUP41 Gene

Mouse

A preferred DNA construct will comprise, from 5'-end to 3'-end: (a) a first nucleotide sequence that is comprised in the mouse RUP41 genomic sequence; (b) a nucleotide sequence comprising a positive selection marker, such as the marker for neomycin resistance (neo); and (c) a second nucleotide sequence that is comprised in the mouse RUP41 genomic sequence and is located on the genome downstream of the first mouse RUP41 nucleotide sequence (a). Mouse RUP41 genomic sequence will be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety). Probes for said isolation of mouse RUP41 genomic sequence will be derived from cDNA encoding a mouse RUP41 polypeptide, wherein said cDNA may be obtained using as template mRNA from mouse heart, lung, or adipose tissue.

In preferred embodiments, this DNA construct also comprises a negative selection marker located upstream the nucleotide sequence (a) or downstream the nucleotide sequence (c). Preferably, the negative selection marker comprises the thymidine kinase (tk) gene [Thomas et al., Cell (1986) 44:419-28], the hygromycin beta gene [Te Riele et al., Nature (1990) 348:649-51], the hprt gene [Van der Lugt et al., Gene (1991) 105:263-7; Reid et al., Proc Natl Acad Sci USA (1990) 87:4299-4303] or the Diptheria toxin A fragment (Dt-A) gene [Nada et al., Cell (1993) 73:1125-35; Yagi et al., Proc Natl Acad Sci USA (1990) 87:9918-9922], which disclosures are hereby incorporated by reference in their entireties. Preferably, the positive selection marker is located within a mouse RUP41 exon sequence so as to interrupt the sequence encoding a mouse RUP41 polypeptide. These replacement vectors are described, for example, by Thomas et al., Cell (1986) 44:419-28; Thomas et al., Cell (1987) 51:503-12; Mansour et al., Nature (1988) 336:348-52; Koller et al., Annu Rev Immunol (1992) 10:705-30; and U.S. Pat. No. 5,631,153; which disclosures are hereby incorporated by reference in their entireties.

The first and second nucleotide sequences (a) and (c) may be indifferently located within a mouse RUP41 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb, and most preferably from 2 to 4 kb.

Methods of making a mouse comprising knockout of a selected gene are well known to those of ordinary skill in the art and have been used to successfully inactivate a wide range of genes.

Rat

Gene targeting technology for the rat is less robust than that for the mouse and is an area of active interest. One approach will be to inactivate rat RUP41 gene in rat embryonic stem cell (ESC)-like cells and then inject cells with inactivated rat RUP41 gene into rat blastocysts generated after fusion of two-cell embryos [Krivokharchenko et al., Mol Reprod Dev (2002) 61:460-5].

The rat gene will be identified by screening a rat genomic library under stringent hybridization conditions using the rat RUP41 polynucleotide of SEQ ID NO:6. Full-length or essentially full-length rat RUP41 cDNA will be identified by screening a rat heart or brain cDNA library under similar conditions. Conditions for stringent nucleic acid hybridization are well known to persons of ordinary skill in the art [Maniatis T, et al. (1982) Molecular Cloning: A Laboratory Manual, Cold Spring Harbor, N.Y.].

An alternative approach will be to inactivate rat RUP41 gene in rat ESC-like cells and then transfer the nucleus of the rat ESC-like cells having inactivated rat RUP41 gene into enucleated oocytes [Sato K et al., Hum Cell (2001) 14:301-4; Wakayama and Yanagimachi, Semin Cell Dev Biol (1999) 10:253-8; Hochedlinger and Jaenisch, Nature (2002) 415: 1035-8; Yanagimachi, Mol Cell Endocrinol (2002) 187:241-8; the disclosures of which are incorporated herein by reference in their entireties].

Methods analogous or alternative [also see, e.g., Zan et al, Nature Biotechnology (2003) 21:645-51; the disclosure of which is hereby incorporated by reference in its entirety] to those described for the mouse may be used to make a rat comprising knockout of RUP41 gene.

Pig

Analogous or alternative methods may be used to make a pig comprising knockout of RUP41 gene [see, e.g., Lai et al., Science (2002) 295:1089-1092; the disclosure of which is hereby incorporated by reference in its entirety].

Cre-LoxP System:

Mouse/Rat/Pig Comprising a Cardiomyocyte-Selective Knockout of RUP41 Gene

Mouse

These new DNA constructs make use of the site specific recombination system of the P1 phage. The P1 phage possesses a recombinase called Cre that interacts with a 34 base pair loxP site. The loxP site is composed of two palindromic sequences of 13 bp separated by an 8 bp conserved sequence [Hoess R H et al, Nucleic Acids Res (1986) 14:2287-300; which disclosure is hereby incorporated by reference in its entirety]. The recombination by the Cre enzyme between two loxP sites having an identical orientation leads to the deletion of the DNA fragment.

The Cre-loxP system used in combination with a homologous recombination technique has been first described by Gu et al. [Gu H et al., Cell (1993) 73:1155-64; Gu H et al., Science (1994) 265:103-6; which disclosures are hereby incorporated by reference in their entirety]. Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as by lipofection of the enzyme into the cells, such as described by Baubonis et al. [Baubonis W and Sauer B, Nucleic Acids Res (1993) 21:2025-9; which disclosure is hereby incorporated by reference in its entirety]; (b) transfecting the cell host with a vector comprising the Cre coding sequence operably linked to a promoter functional in the recombinant cell host, which promoter being optionally inducible, said vector being introduced in the recombinant cell host, such as described by Gu et al. [Gu H et al., Cell (1993) 73:1155-64; which disclosure is hereby incorporated by reference in its entirety] and Sauer et al. [Sauer B and Henderson N, Proc Natl Acad Sci USA (1988) 85:5166-70; which disclosure is hereby incorporated by reference in its entirety]; (c) introducing into the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. [Gu H et al., Science (1994) 265:103-6; the disclosure of which is hereby incorporated by reference in its entirety].

Vectors and methods using the Cre-loxP system are described, e.g., by Zou et al. (1994); Minamisawa S et al., J Biol Chem (1999) 274:10066-70; Chen et al., J Biol Chem (1998) 273:1252-6; Chen et al., Development (1998) 125: 1943-9; the disclosure of each of which is hereby incorporated by reference in its entirety.

In preferred embodiments of the invention, Cre is introduced into the genome of the cell host by strategy (c) above, wherein said promoter is cardiomyocyte selective and leads to cardiomyocyte-selective disruption of (loxP-flanked; "floxed") mouse RUP41 genomic sequence. In some embodiments, said cardiomyocyte-selective promoter is that for the ventricular specific isoform of myosin light chain 2 (mlc-2v) [Minamisawa S et al., J Biol Chem (1999) 274:10066-70; Chen et al., J Biol Chem (1998) 273:1252-6; the disclosure of each of which is hereby incorporated by reference in its entirety]. Transgenic mice comprising insertion of Cre recombinase coding sequence into the endogenous mlc-2v locus ("mlc-2v cre knock-in mice") have been described [Chen et al., Development (1998) 125:1943-9; the disclosure of which is hereby incorporated by reference in its entirety]. Methods for floxing a selected gene are within the purview of those of ordinary skill in the art [see, e.g., Chen et al., Development (1998) 125:1943-9].

In some embodiments, the invention features a method of making a mouse comprising a cardiomyocyte-selective knockout of RUP41 gene, comprising crossing the mlc-2 cre allele, supra, with a floxed RUP41 gene.

Other methods of making a mouse comprising a cardiomyocyte-selective knockout of RUP41 gene are well known to persons of ordinary skill in the art; see, e.g, Kuhn R and Torres R M, Methods Mol Biol (2002) 180:175-204; Sauer B, Methods (1998) 14:381-92; Gutstein D E et al., Circulation Research (2001) 88:333; Minamino T et al., Circulation Research (2001) 88:587; and Bex A et al., J Urol (2002) 168:2641-2644; the disclosure of each of which is hereby incorporated by reference in its entirety.

Rat

Analogous or alternative [see, e.g., Zan et al, Nature Biotechnology (2003) 21:645-51; the disclosure of which is hereby incorporated by reference in its entirety] methods may be used to make a rat comprising a cardiomyocyte knockout of RUP41 gene.

Pig

Analogous or alternative methods may be used to make a pig comprising a cardiomyocyte-selective knockout of RUP41 gene [see, e.g., Lai et al., Science (2002) 295:1089-1092; the disclosure of which is hereby incorporated by reference in its entirety].

Throughout this application, various publications, patents and published patent applications are cited. The disclosures of these publications, patents and published patent applications referenced in this application are hereby incorporated by reference in their entirety into the present disclosure. Modifications and extension of the disclosed inventions that are within the purview of the skilled artisan are encompassed within the above disclosure and the claims that follow.

What is claimed:

1. A method of identifying a compound as having cardioprotective activity comprising:
    (a) contacting a candidate compound with a G protein-coupled receptor (GPCR) comprising an amino acid sequence having at least 95% identity to SEQ ID NO:3, wherein said GPCR is present on a cell or isolated membrane thereof and wherein overexpression of the GPCR promotes survival of cardiomyocytes;
    (b) determining whether said compound stimulates the GPCR;
    (c) identifying a compound as having an activity that stimulates said GPCR;
    (d) determining whether said compound of step (c) has cardioprotective activity by:
        (i) administering said compound of step (c) to a mammal; and
        (ii) determining whether said compound of step (c) modulates cardiac function in the mammal; or
        (iii) contacting said compound of step (c) with a cardiomyocyte cell in vitro; and
        (iv) determining whether said compound modulates survival of said cardiomyocyte cell; and
    (e) identifying a compound as having cardioprotective activity.

2. The method of claim 1, wherein said cell is a mammalian cell, a yeast cell or a melanophore cell.

3. The method of claim 1, wherein said G protein-coupled receptor is constitutively active.

4. The method of claim 1, wherein said G protein-coupled receptor comprises the amino acid sequence of an endogenous receptor comprising the amino acid sequence of SEQ ID NO:2, SEQ ID NO:3 or SEQ ID NO:5.

5. The method of claim 1, wherein step (b) of the method comprises detecting a second messenger.

6. The method of claim 5, wherein the second messenger is cAMP or $IP_3$.

7. The method of claim 1, wherein step (b) of the method comprises measuring pigment distribution in melanophore assay.

8. The method of claim 1, wherein step (b) of the method comprises measuring GTPγS binding to membrane.

9. The method of claim 1, wherein the method comprises measuring apoptosis of the cardiomyocyte cell.

10. The method of claim 1, wherein the mammal is a rat or mouse model of heart disease.

11. The method of claim 1, wherein step (d)(ii) of said method comprises evaluating a cardiovascular disorder, an ischemic heart disease, or a cardiovascular function in said mammal.

12. The method of claim 1, wherein step (d)(ii) of said method comprises evaluating said mammal for congestive heart failure.

13. The method of claim 1, wherein the compound of step (c) is an agonist of the GPCR.

14. The method of claim 13, wherein the agonist is a partial agonist.

* * * * *

SEQUENCE LISTING

```
<160> NUMBER OF SEQ ID NOS: 12

<210> SEQ ID NO 1
<211> LENGTH: 1881
<212> TYPE: DNA
<213> ORGANISM: Homo sapien

<400> SEQUENCE: 1
gttatttctt caaaaggaaa acacaatttt cttttatatc aaaacaatgc aaacttgatg      60
gttcttaatt ctacattttc tattaatagt ttacaaactt aaaaattaaa ctaagtacac     120
aattgaaaga ttttttttc ttacaaagaa cacgttatac gtcatttaaa ttgccaaata     180
tcaaatagtt tattctattt cactttctag ggaaaaaaac caactgctcc aaaagaatgt     240
gtttttctcc cattctggaa atcaacatgc agtctgaatc taacattaca gtgcgagatg     300
acattgatga catcaacacc aatatgtacc aaccactatc atatccgtta agctttcaag     360
tgtctctcac cggatttctt atgttagaaa ttgtgttggg acttggcagc aacctcactg     420
tattggtact ttactgcatg aaatccaact taatcaactc tgtcagtaac attattacaa     480
tgaatcttca tgtacttgat gtaataattt gtgtgggatg tattcctcta actatagtta     540
tccttctgct ttcactggag agtaacactg ctctcatttg ctgtttccat gaggcttgtg     600
tatcttttgc aagtgtctca acagcaatca acgttttgc tatcactttg gacagatatg     660
acatctctgt aaaacctgca aaccgaattc tgacaatggg cagagctgta atgttaatga     720
tatccatttg gatttttttct tttttctctt tcctgattcc ttttattgag gtaaatttt      780 tcagtcttca aagtggaaat acctgggaaa acaagacact tttatgtgtc agtacaaatg     840
aatactacac tgaactggga atgtattatc acctgttagt acagatccca atattctttt     900
tcactgttgt agtaatgtta atcacataca ccaaaatact tcaggctctt aatattcgaa     960
taggcacaag attttcaaca gggcagaaga agaaagcaag aaagaaaaag acaatttctc    1020
taaccacaca acatgaggct acagacatgt cacaaagcag tggtgggaga aatgtagtct    1080
ttggtgtaag aacttcagtt tctgtaataa ttgccctccg gcgagctgtg aaacgacacc    1140
gtgaacgacg agaaagacaa aagagagtct tcaggatgtc tttattgatt atttctacat    1200
ttcttctctg ctggacacca atttctgttt taaataccac catttatgt ttaggcccaa     1260 gtgacctttt agtaaaatta agattgtgtt ttttagtcat ggcttatgga acaactatat    1320
ttcaccctct attatatgca ttcactagac aaaaatttca aaggtcttg aaaagtaaaa     1380
```

```
tgaaaaagcg agttgtttct atagtagaag ctgatcccct gcctaataat gctgtaatac   1440
acaactcttg gatagatccc aaaagaaaca aaaaaattac ctttgaagat agtgaaataa   1500
gagaaaaacg tttagtgcct caggttgtca cagactagag aaaagtctca gtttcaccaa   1560
atccacattc aaatgagttt taaatttaaa ttgtaaaaac tgatattact gccaaatata   1620
agaaaaatat tttaagtatt ggttatgttg taaattttca atgtgaaatg ctaattagat   1680
aggtcatata tattcaattt cttcattact taatgtattt gttgcatggc agtttgttaa   1740
agtactatca tgtgtatatt ttgtcaatat tatgtccaac agaaaatatt catgtaagtc   1800
atatttttta aggaataaat acatagcctt aaaacagtgt ataactttaa aatgtaaaaa   1860
aaaaaaaaaa aaaaaaaaaa a                                             1881

<210> SEQ ID NO 2
<211> LENGTH: 433
<212> TYPE: PRT
<213> ORGANISM: Homo sapien

<400> SEQUENCE: 2

Met Cys Phe Ser Pro Ile Leu Glu Ile Asn Met Gln Ser Glu Ser Asn
1               5                   10                  15

Ile Thr Val Arg Asp Asp Ile Asp Ile Asn Thr Asn Met Tyr Gln
            20                  25                  30

Pro Leu Ser Tyr Pro Leu Ser Phe Gln Val Ser Leu Thr Gly Phe Leu
        35                  40                  45

Met Leu Glu Ile Val Leu Gly Leu Gly Ser Asn Leu Thr Val Leu Val
    50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Ile Cys Val Gly Cys Ile
                85                  90                  95

Pro Leu Thr Ile Val Ile Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205

Met Tyr Tyr His Leu Leu Val Gln Ile Pro Ile Phe Phe Phe Thr Val
    210                 215                 220

Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Ala Arg Lys
                245                 250                 255

Lys Lys Thr Ile Ser Leu Thr Thr Gln His Glu Ala Thr Asp Met Ser
        260                 265                 270

Gln Ser Ser Gly Gly Arg Asn Val Val Phe Gly Val Arg Thr Ser Val
```

-continued

```
                275                 280                 285
Ser Val Ile Ile Ala Leu Arg Arg Ala Val Lys Arg His Arg Glu Arg
        290                 295                 300

Arg Glu Arg Gln Lys Arg Val Phe Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
                340                 345                 350

Leu Val Met Ala Tyr Gly Thr Thr Ile Phe His Pro Leu Leu Tyr Ala
                355                 360                 365

Phe Thr Arg Gln Lys Phe Gln Lys Val Leu Lys Ser Lys Met Lys Lys
                370                 375                 380

Arg Val Val Ser Ile Val Glu Ala Asp Pro Leu Pro Asn Asn Ala Val
385                 390                 395                 400

Ile His Asn Ser Trp Ile Asp Pro Lys Arg Asn Lys Lys Ile Thr Phe
                    405                 410                 415

Glu Asp Ser Glu Ile Arg Glu Lys Arg Leu Val Pro Gln Val Val Thr
                420                 425                 430

Asp

<210> SEQ ID NO 3
<211> LENGTH: 433
<212> TYPE: PRT
<213> ORGANISM: Homo sapien

<400> SEQUENCE: 3

Met Cys Phe Ser Pro Ile Leu Glu Ile Asn Met Gln Ser Glu Ser Asn
1               5                   10                  15

Ile Thr Val Arg Asp Asp Ile Asp Asp Ile Asn Thr Asn Met Tyr Gln
                20                  25                  30

Pro Leu Ser Tyr Pro Leu Ser Phe Gln Val Ser Leu Thr Gly Phe Leu
            35                  40                  45

Met Leu Glu Ile Val Leu Gly Leu Gly Ser Asn Leu Thr Val Leu Val
        50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Cys Val Gly Cys Ile
                85                  90                  95

Pro Leu Thr Ile Val Ile Leu Leu Ser Leu Glu Ser Asn Thr Ala
                100                 105                 110

Leu Ile Cys Cys Phe His Glu Ala Cys Val Ser Phe Ala Ser Val Ser
            115                 120                 125

Thr Ala Ile Asn Val Phe Ala Ile Thr Leu Asp Arg Tyr Asp Ile Ser
        130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Phe Ser Phe Leu Ile Pro Phe
                    165                 170                 175

Ile Glu Val Asn Phe Phe Ser Leu Gln Ser Gly Asn Thr Trp Glu Asn
                180                 185                 190

Lys Thr Leu Leu Cys Val Ser Thr Asn Glu Tyr Tyr Thr Glu Leu Gly
            195                 200                 205

Met Tyr Tyr His Leu Leu Val Gln Ile Pro Ile Phe Phe Phe Thr Val
```

-continued

```
                210                 215                 220
Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Ala Arg Lys
                245                 250                 255

Lys Lys Thr Ile Ser Leu Thr Thr Gln His Glu Ala Thr Asp Met Ser
                260                 265                 270

Gln Ser Ser Gly Gly Arg Asn Val Val Phe Gly Val Arg Thr Ser Val
                275                 280                 285

Ser Val Ile Ile Ala Leu Arg Arg Ala Val Lys Arg His Arg Glu Arg
                290                 295                 300

Arg Glu Arg Gln Lys Arg Val Phe Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
                340                 345                 350

Leu Val Met Ala Tyr Gly Thr Thr Ile Phe His Pro Leu Leu Tyr Ala
                355                 360                 365

Phe Thr Arg Gln Lys Phe Gln Lys Val Leu Lys Ser Lys Met Lys Lys
                370                 375                 380

Arg Val Val Ser Ile Val Glu Ala Asp Pro Leu Pro Asn Asn Ala Val
385                 390                 395                 400

Ile His Asn Ser Trp Ile Asp Pro Lys Arg Asn Lys Lys Ile Thr Phe
                405                 410                 415

Glu Asp Ser Glu Ile Arg Glu Lys Cys Leu Val Pro Gln Val Val Thr
                420                 425                 430

Asp

<210> SEQ ID NO 4
<211> LENGTH: 1269
<212> TYPE: DNA
<213> ORGANISM: Mouse

<400> SEQUENCE: 4
atgcagtctg aatcaaacgt cacggtgcga gatgacattg atgacatcga caccaatatg      60
taccaaccac tgtcataccc actaagcttt caagtgtctc tcactggatt tctcatgtta     120
gagatcgtgc tggggcttgg cagcaacctt accgtcctgg tactttactg catgaaatcc     180
aacttaatca actctgtcag taacattatt acaatgaacc tccatgtact tgatgtcata     240
atttgtgtgg gatgcattcc tctaactata gtgatccttc tgctctcact ggagagtaac     300
actgctctca tctgctgttt ccacgaagct tgtgtttcct ttgcaagtgt ttcgacagca     360
atcaacgttt tgctattac tctggacaga tatgacatct ctgtaaaacc tgcaaacaga     420
attctgacaa tgggcagagc tgtaatgcta atgacatcca tttggatttt tctttcttc     480 tcattcctga ttcccttcat tgaagtaaat ttttcagtc ttcaaagtgg aaatacatgg     540
gcaaacaaga cactgctgtg tgtcagtaca agtgaatact atactgagct cgggatgtac     600
tatcaccttt tggtgcagat ccccatcttc ttcttcacag ttatagtcat gttgatcaca     660
tacactaaga tactccaggc tcttaacatc cgcataggca ctagattctc aacaggacag     720
aagaagaaag cccgaaagaa aaagacaatc tctctagcta cacatgagac cacagacatg     780
tcacaaagca gtggtgggag gaatgtcgtg tttggtgtga gaacttcagt ttctgtaata     840
```

```
attgccctcc ggcgagccgt gaaacgccac cgggaacgac gagaacggca gaaaagagtc    900
ttcaaaatgt cgttattgat tatttctaca tttcttctct gttggacacc aatttctgtt    960
ttaaatacca ccattctatg tttaggccca agtgaccttt tagtaaaatt aagattgtgt   1020
tttctagtca tggcttatgg aacaacgata ttccaccctc tcttgtatgc attcaccaga   1080
caaaagtttc aaaaggtctt aaagagtaag atgaaaaagc gagttgtttc catagttgaa   1140
gctgatccca tgcctaataa cgctgtaata cacaactcat ggatagatcc taaaagaaac   1200
aaaaaggtta cctatgaaga cagtgaaata agagagaaat gtttagtacc tcaggttgtc   1260
acagactag                                                            1269
```

<210> SEQ ID NO 5
<211> LENGTH: 422
<212> TYPE: PRT
<213> ORGANISM: Mouse

<400> SEQUENCE: 5

```
Met Gln Ser Glu Ser Asn Val Thr Val Arg Asp Asp Ile Asp Asp Ile
1               5                   10                  15

Asp Thr Asn Met Tyr Gln Pro Leu Ser Tyr Pro Leu Ser Phe Gln Val
            20                  25                  30

Ser Leu Thr Gly Phe Leu Met Leu Glu Ile Val Leu Gly Leu Gly Ser
        35                  40                  45

Asn Leu Thr Val Leu Val Leu Tyr Cys Met Lys Ser Asn Leu Ile Asn
    50                  55                  60

Ser Val Ser Asn Ile Ile Thr Met Asn Leu His Val Leu Asp Val Ile
65                  70                  75                  80

Ile Cys Val Gly Cys Ile Pro Leu Thr Ile Val Ile Leu Leu Leu Ser
                85                  90                  95

Leu Glu Ser Asn Thr Ala Leu Ile Cys Cys Phe His Glu Ala Cys Val
            100                 105                 110

Ser Phe Ala Ser Val Ser Thr Ala Ile Asn Val Phe Ala Ile Thr Leu
        115                 120                 125

Asp Arg Tyr Asp Ile Ser Val Lys Pro Ala Asn Arg Ile Leu Thr Met
    130                 135                 140

Gly Arg Ala Val Met Leu Met Thr Ser Ile Trp Ile Phe Ser Phe Phe
145                 150                 155                 160

Ser Phe Leu Ile Pro Phe Ile Glu Val Asn Phe Phe Ser Leu Gln Ser
                165                 170                 175

Gly Asn Thr Trp Ala Asn Lys Thr Leu Leu Cys Val Ser Thr Ser Glu
            180                 185                 190

Tyr Tyr Thr Glu Leu Gly Met Tyr Tyr His Leu Leu Val Gln Ile Pro
        195                 200                 205

Ile Phe Phe Phe Thr Val Ile Val Met Leu Ile Thr Tyr Thr Lys Ile
    210                 215                 220

Leu Gln Ala Leu Asn Ile Arg Ile Gly Thr Arg Phe Ser Thr Gly Gln
225                 230                 235                 240

Lys Lys Lys Ala Arg Lys Lys Lys Thr Ile Ser Leu Ala Thr His Glu
                245                 250                 255

Thr Thr Asp Met Ser Gln Ser Ser Gly Gly Arg Asn Val Val Phe Gly
            260                 265                 270

Val Arg Thr Ser Val Ser Val Ile Ile Ala Leu Arg Arg Ala Val Lys
        275                 280                 285

Arg His Arg Glu Arg Arg Glu Arg Gln Lys Arg Val Phe Lys Met Ser
```

```
            290              295              300
Leu Leu Ile Ile Ser Thr Phe Leu Leu Cys Trp Thr Pro Ile Ser Val
305                 310                 315                 320

Leu Asn Thr Thr Ile Leu Cys Leu Gly Pro Ser Asp Leu Leu Val Lys
                325                 330                 335

Leu Arg Leu Cys Phe Leu Val Met Ala Tyr Gly Thr Thr Ile Phe His
            340                 345                 350

Pro Leu Leu Tyr Ala Phe Thr Arg Gln Lys Phe Gln Lys Val Leu Lys
        355                 360                 365

Ser Lys Met Lys Lys Arg Val Val Ser Ile Val Glu Ala Asp Pro Met
370                 375                 380

Pro Asn Ala Val Ile His Asn Ser Trp Ile Asp Pro Lys Arg Asn
385                 390                 395                 400

Lys Lys Val Thr Tyr Glu Asp Ser Glu Ile Arg Glu Lys Cys Leu Val
                405                 410                 415

Pro Gln Val Val Thr Asp
            420

<210> SEQ ID NO 6
<211> LENGTH: 542
<212> TYPE: DNA
<213> ORGANISM: Rat
<220> FEATURE:
<221> NAME/KEY: misc_feature
<222> LOCATION: (514)..(514)
<223> OTHER INFORMATION: n is a, c, g, or t

<400> SEQUENCE: 6
atgcatgctc gagcggccgc cagtgtgatg gatatctgca gaattcgccc ttgtaataat      60
tgccctccgg cgagccgtga acgacaccg ggaacgacga gagaggcaga aaagagtctt     120
caaaaatgtc gttatggata atttctacat ttcttctctg ttggacacca atttctgttt     180
taaataccac cattttatgt ttaggcccaa gtgacctttt agtaaaatta agattgtgtt     240
ttctagtcat ggcttatgga acaactatat tccatcctct cctgtatgca ttcaccagac     300
aaaaatttca aaggtctta aaaagtaaga tgaaaaagcg agttgtttcc atagttgaag     360
ctgatcccat gcctaataac gctgtaatac acaactcatg gatagatcct aaaagaaaca     420
aaaaggttac ctacgaagac agtgaaataa gagagaaatg tttagtacct caggttgtca     480
cagactagaa gggcgaattc cagcacactg gcgnccgtta ctagtggatc cgagctcggt     540
ac                                                                    542

<210> SEQ ID NO 7
<211> LENGTH: 30
<212> TYPE: DNA
<213> ORGANISM: Artificial
<220> FEATURE:
<223> OTHER INFORMATION: Novel Sequence

<400> SEQUENCE: 7
tcccccggga aaaaaccaa ctgctccaaa                                        30

<210> SEQ ID NO 8
<211> LENGTH: 31
<212> TYPE: DNA
<213> ORGANISM: Artificial
<220> FEATURE:
<223> OTHER INFORMATION: Novel Sequence

<400> SEQUENCE: 8
```

```
taggatccat ttgaatgtgg atttggtgaa a                               31

<210> SEQ ID NO 9
<211> LENGTH: 36
<212> TYPE: DNA
<213> ORGANISM: Artificial
<220> FEATURE:
<223> OTHER INFORMATION: Novel Sequence

<400> SEQUENCE: 9
gatcaagctt ccatggcgtg ctgcctgagc gaggag                          36

<210> SEQ ID NO 10
<211> LENGTH: 53
<212> TYPE: DNA
<213> ORGANISM: Artificial
<220> FEATURE:
<223> OTHER INFORMATION: Novel Sequence

<400> SEQUENCE: 10
gatcggatcc ttagaacagg ccgcagtcct tcaggttcag ctgcaggatg gtg       53

<210> SEQ ID NO 11
<211> LENGTH: 23
<212> TYPE: DNA
<213> ORGANISM: Artificial
<220> FEATURE:
<223> OTHER INFORMATION: Novel Sequence

<400> SEQUENCE: 11
gtaataattg ccctccggcg agc                                        23

<210> SEQ ID NO 12
<211> LENGTH: 21
<212> TYPE: DNA
<213> ORGANISM: Artificial
<220> FEATURE:
<223> OTHER INFORMATION: Novel Sequence

<400> SEQUENCE: 12
ctagtctgtg acaacctgag g                                          21
```